United States Patent
Niimi et al.

(10) Patent No.: US 9,051,569 B2
(45) Date of Patent: Jun. 9, 2015

(54) INSECT PEST CONTROL METHOD

(75) Inventors: Teruyuki Niimi, Nagoya (JP); Hirofumi Yoshioka, Nagoya (JP); Yutaka Sato, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 712 days.

(21) Appl. No.: 13/375,842

(22) PCT Filed: Jun. 4, 2010

(86) PCT No.: PCT/JP2010/059499
§ 371 (c)(1),
(2), (4) Date: Mar. 1, 2012

(87) PCT Pub. No.: WO2010/140675
PCT Pub. Date: Dec. 9, 2010

(65) Prior Publication Data
US 2012/0151631 A1 Jun. 14, 2012

(30) Foreign Application Priority Data
Jun. 5, 2009 (JP) ................................. 2009-136701

(51) Int. Cl.
*A01N 61/00* (2006.01)
*C12N 15/113* (2010.01)
*A01N 43/90* (2006.01)
*A01N 63/00* (2006.01)
*C12N 15/82* (2006.01)

(52) U.S. Cl.
CPC .............. *C12N 15/113* (2013.01); *A01N 43/90* (2013.01); *A01N 61/00* (2013.01); *A01N 63/00* (2013.01); *C12N 15/8286* (2013.01); *C12N 2310/14* (2013.01)

(58) Field of Classification Search
None
See application file for complete search history.

(56) References Cited

U.S. PATENT DOCUMENTS

2006/0272049 A1* 11/2006 Waterhouse et al. ......... 800/279

FOREIGN PATENT DOCUMENTS

| JP | 3033959 B2 | 5/1987 |
| JP | 3532943 B2 | 7/1994 |
| JP | 2002-15923 A | 6/2002 |
| WO | WO-2005/049841 A1 | 6/2005 |

OTHER PUBLICATIONS

Baum, J.A. et al., "Control of coleopteran insect pests through RNA interference," Nat. Biotechnol. vol. 25, Nov. 2007, pp. 1322-1326.
Mao, Y.-B. et al., "Silencing a cotton bollworm P450 monooxygenase gene by plant-mediated RNAi impairs larval tolerance of gossypol," Nat. Biotechnol. vol. 25, Nov. 2007, pp. 1307-1313.
Price, D.R.G. et al., "RNAi-mediated crop protection against insects," Trends in Biotechnology vol. 26 No. 7, May 2008, pp. 393-400.
Whangbo, J.S. et al., "Environmental RNA interference," Trends in Genetics vol. 24 No. 6, Apr. 2008, pp. 297-305.
International Search Report dated Aug. 10, 2010, issued for PCT/JP2010/059499.
Pridgeon, Julia W. et al., "Topically applied *AaeIAP1* double-stranded RNA kills female adults of *Aedes aegypti*," Journal of Medical Entomology, vol. 45, No. 3, May 2008, pp. 414-420.
Supplementary European Search Report dated Sep. 3, 2013, issued for the corresponding European patent application No. 10783457.4.

* cited by examiner

*Primary Examiner* — David T Fox
*Assistant Examiner* — Stephen Uyeno
(74) *Attorney, Agent, or Firm* — Locke Lord LLP

(57) ABSTRACT

The present invention is intended to provide means of pest control which achieve marked pest control effect. The pest control effect is achieved by the incorporation of an inhibitor (IAP inhibitor) against inhibitor of apoptosis (IAP) into the body of the target pest. The expression of the IAP is preferably inhibited by RNAi.

6 Claims, 6 Drawing Sheets

FIG. 1

Change over time after initiation of ingestion

| Time elapsed after initiation of ingestion | Changes |
|---|---|
| 0 h | All individuals were third instar, 1 day old |
| 12 h | All the individuals of the Hv-iap RNAi group were slow-moving. The amount of ingestion was small in all the individuals of the Hv-iap RNAi group. |
| 36 h | All the individuals of the Hv-iap RNAi group stopped ingestion. All the individuals of the $H_2O$ group stopped ingestion immediately before molting. |
| 48~60 h | All the individuals of the $H_2O$ group molted into fourth instar. |

FIG. 2
64 hours after initiation of ingestion
Hv-iap dsRNA
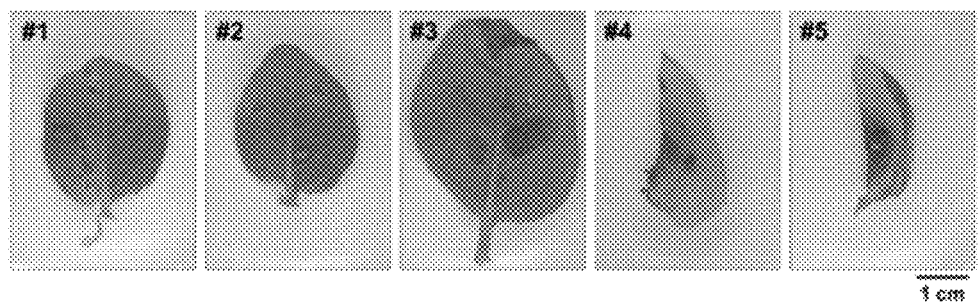
H₂O
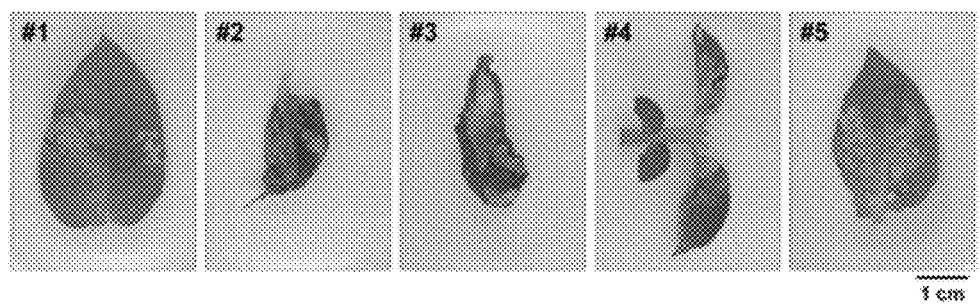

*FIG. 3*

Time elapsed from initiation of ingestion to death

| | | |
|---|---|---|
| | #1 | 63 h |
| | #2 | 84 h |
| Hv-iap dsRNA | #3 | 66 h |
| | #4 | 84 h |
| | #5 | 59 h |
| | #1 | Alive |
| | #2 | Alive |
| $H_2O$ | #3 | Alive |
| | #4 | Alive |
| | #5 | Alive |

*FIG. 4*

| Har-iap dsRNA | #1 | 47 h |
|---|---|---|
| | #2 | 93 h |
| | #3 | 24 h |
| GFP dsRNA | #1 | Alive |
| | #2 | Alive |
| | #3 | Alive |

*FIG. 5*

| Bt-iap dsRNA | 8 h | 11 h | 24 h | 30 h | 48 h |
|---|---|---|---|---|---|
| #1 | Moving | Moving | Moderately moving | Slightly moving | Dead |
| #2 | Moving | Moving | Dead | | |
| #3 | Actively moving | Moving | Dead | | |
| #4 | Actively moving | Moving | Slightly moving | Slightly moving | Dead |
| #5 | Moving | Moving | Dead | | |
| #6 | Moving | Moving | Dead | | |
| #7 | Moving | Moderately moving | Dead | | |
| #8 | Moving | Slightly moving | Dead | | |
| #9 | Moving | Slightly moving | Dead | | |
| #10 | Actively moving | Moderately moving | Dead | | |

| DsRed dsRNA | 8 h | 11 h | 24 h | 30 h | 48 h |
|---|---|---|---|---|---|
| #1 | Actively moving | Actively moving | Actively moving | Actively moving | Actively moving |
| #2 | Actively moving | Actively moving | Actively moving | Actively moving | Actively moving |
| #3 | Actively moving | Actively moving | Actively moving | Actively moving | Actively moving |
| #4 | Actively moving | Actively moving | Actively moving | Actively moving | Actively moving |
| #5 | Actively moving | Actively moving | Actively moving | Actively moving | Actively moving |
| #6 | Actively moving | Actively moving | Actively moving | Actively moving | Actively moving |
| #7 | Actively moving | Actively moving | Actively moving | Actively moving | Actively moving |
| #8 | Actively moving | Actively moving | Actively moving | Actively moving | Actively moving |
| #9 | Actively moving | Actively moving | Actively moving | Actively moving | Actively moving |
| #10 | Actively moving | Actively moving | Actively moving | Actively moving | Actively moving |

FIG. 6

| | | 23 h | 43 h | 62 h | 67 h |
|---|---|---|---|---|---|
| HV-iap synthetic dsRNA, 20 ng | #1 | Stopped ingestion | Stopped ingestion | Stopped ingestion | Stopped ingestion |
| | #2 | Stopped ingestion | Stopped ingestion | Stopped ingestion | Stopped ingestion |
| | #3 | Stopped ingestion | Stopped ingestion | Stopped ingestion | Stopped ingestion |
| | #4 | Stopped ingestion | Stopped ingestion | Stopped ingestion | Stopped ingestion |
| RNA extracted from leaves affected with HV-iap dsRNA-introduced virus, 2 μg | #1 | Ingested normally | Almost stopped | Almost stopped | Stopped ingestion |
| | #2 | Ingested normally | Almost stopped | Almost stopped | Stopped ingestion |
| | #3 | Ingested normally | Almost stopped | Almost stopped | Stopped ingestion |
| | #4 | Ingested normally | Ingested normally | Ingested normally | Ingested normally |
| RNA extracted from virus-affected leaves, 2 μg | #1 | Ingested normally | Ingested normally | Ingested normally | Ingested normally |
| | #2 | Ingested normally | Ingested normally | Ingested normally | Ingested normally |
| | #3 | Ingested normally | Ingested normally | Ingested normally | Ingested normally |
| | #4 | Ingested normally | Ingested normally | Ingested normally | Ingested normally |

SEQUENCE LISTING

```
<160> NUMBER OF SEQ ID NOS: 27

<210> SEQ ID NO 1
<211> LENGTH: 1790
<212> TYPE: DNA
<213> ORGANISM: Henosepilachna vigintioctopunctata

<400> SEQUENCE: 1
ggtaaatgtc atggttatgc aaggaagtaa ccatcccgtg tttatgttta tattactagt      60
tcgtttcaat tactctaaaa tttgtagtgg atataatcaa gataattgtt ctggctttac     120
gatttctgca actcataagt tttaaacctc gcattcgaaa atggttccac cagtagaagt     180
attgtcttat ccaagctcga ctaggaagtt tggtaacgga cttgatttga agaatatgcc     240
cgcagcagta agtgtgaaga gaaatataaa tcataccata ggaaaagaca ctggcgataa     300
tggttgttcc tttttgaatc taactccacc cgcaaattta ttggctacga tcgagggacg     360
cctgaagacg tacaaaaatt ggcccaacaa gaatatagat ccccagaagt tagcggccgc     420
cggctttttc tattctggaa aaactgacat cgtcgagtgt ttcaagtgcg gtatcaaggg     480
acacaactgg ttgttgaacg acgatccaat ggaagatcac aaaaaatgga ataggaattg     540
ttcttttgta agagaaaacg cacccgaaga aaataacgtc ccacaaactg gcaccggtag     600
tgattattgt ggcaatttag acgtcgtaac ctcacaatat acagtcagcg aagaacctgg     660
agattattat cgtaacttgg gtgtggacat ctctccgttc ttgcaaactg gcgctaaaac     720
gaatcagtcc gagggtcata acctggaggg gttgttacta agaacgagga agggcccaag     780
tcacccagat cagatcattt acgagcgtag agtggcgaca ttcgcgaatt ggcccaagtc     840
cttgaaacag aaacccacgg acttggcggc cgcaggcttt tactacctcg gaatcggcga     900
ccagacgttg tgcttttact gcggcggcgg tctgaaagat tgggtcgaag aagacgatcc     960
gtgggaacag cacgcgcttt ggttcccccca gtgtaattat ctattattga agaaaacacc    1020
cgctttcgtc aaagacgtcc aagaaaaaca taaaggcgat ttgtcgtcat ccaagcaaaa    1080
cgagaccgaa gtggtagcaa gtagtagcag tagtcacaac tccaaagaat ctccaagtgc    1140
```

```
ggtggtagaa gagcgagaaa gaaacaacgc agaggaaagc tcgacattat gcaaaatatg   1200
ttataaaaat gaattggctg ttgtatttct accttgcggt catatggtag cttgtgtaga   1260
ttgtgcatca ggattaaaag aatgtgctat ttgccgtaaa gagatccaag ctaatgttcg   1320 agccttttg tcatagttcg cgaacagtta acagtaacag ttactgcttg accacactca    1380
ttttcaaaga agtatggtcg aattatgtct ccagctcaaa atcaccacca aacagtgaca   1440
cgttgtggat gcatttgtgt ttcgacaatt acaggtgggt tctcagaacc ctaaaagtgg   1500
cagttttggc gattaacaaa cccatctagg tgaaaatgtg ctgcgtcgct cacgaagatt   1560
ttgctcgaaa tacagcattc ccttttgatg ccgtatgttg caaactttct tcactgtgca   1620
tgggcaaaag gcttcagttg ttgtgattat tgaatttggc aagcatgagg acacagatct   1680
ttactgatta tacgctgtag agagcttctt gaaatttgaa attcttgtcc acgacgtcga   1740
attgagattc ctggattgtc actgacactt cgacgtacta ctgtgatttt                1790
```

<210> SEQ ID NO 2
<211> LENGTH: 391
<212> TYPE: PRT
<213> ORGANISM: Henosepilachna vigintioctopunctata

<400> SEQUENCE: 2

```
Met Val Pro Pro Val Glu Val Leu Ser Tyr Pro Ser Ser Thr Arg Lys
1               5                   10                  15

Phe Gly Asn Gly Leu Asp Leu Lys Asn Met Pro Ala Ala Val Ser Val
            20                  25                  30

Lys Arg Asn Ile Asn His Thr Ile Gly Lys Asp Thr Gly Asp Asn Gly
        35                  40                  45

Cys Ser Phe Leu Asn Leu Thr Pro Pro Ala Asn Leu Leu Ala Thr Ile
    50                  55                  60

Glu Gly Arg Leu Lys Thr Tyr Lys Asn Trp Pro Asn Lys Asn Ile Asp
65                  70                  75                  80

Pro Gln Lys Leu Ala Ala Ala Gly Phe Phe Tyr Ser Gly Lys Thr Asp
                85                  90                  95

Ile Val Glu Cys Phe Lys Cys Gly Ile Lys Gly His Asn Trp Leu Leu
            100                 105                 110

Asn Asp Asp Pro Met Glu Asp His Lys Lys Trp Asn Arg Asn Cys Ser
        115                 120                 125

Phe Val Arg Glu Asn Ala Pro Glu Glu Asn Asn Val Pro Gln Thr Gly
    130                 135                 140

Thr Gly Ser Asp Tyr Cys Gly Asn Leu Asp Val Val Thr Ser Gln Tyr
145                 150                 155                 160

Thr Val Ser Glu Glu Pro Gly Asp Tyr Tyr Arg Asn Leu Gly Val Asp
                165                 170                 175

Ile Ser Pro Phe Leu Gln Thr Gly Ala Lys Thr Asn Gln Ser Glu Gly
            180                 185                 190

His Asn Leu Glu Gly Leu Leu Leu Arg Thr Arg Lys Gly Pro Ser His
        195                 200                 205

Pro Asp Gln Ile Ile Tyr Glu Arg Arg Val Ala Thr Phe Ala Asn Trp
    210                 215                 220

Pro Lys Ser Leu Lys Gln Lys Pro Thr Asp Leu Ala Ala Ala Gly Phe
225                 230                 235                 240

Tyr Tyr Leu Gly Ile Gly Asp Gln Thr Leu Cys Phe Tyr Cys Gly Gly
                245                 250                 255
```

```
Gly Leu Lys Asp Trp Val Glu Glu Asp Pro Trp Glu Gln His Ala
            260                 265                 270
Leu Trp Phe Pro Gln Cys Asn Tyr Leu Leu Lys Lys Thr Pro Ala
            275                 280                 285
Phe Val Lys Asp Val Gln Glu Lys His Lys Gly Asp Leu Ser Ser Ser
            290                 295                 300
Lys Gln Asn Glu Thr Glu Val Val Ala Ser Ser Ser Ser His Asn
305                 310                 315                 320
Ser Lys Glu Ser Pro Ser Ala Val Val Glu Glu Arg Glu Arg Asn Asn
                325                 330                 335
Ala Glu Glu Ser Ser Thr Leu Cys Lys Ile Cys Tyr Lys Asn Glu Leu
            340                 345                 350
Ala Val Val Phe Leu Pro Cys Gly His Met Val Ala Cys Val Asp Cys
            355                 360                 365
Ala Ser Gly Leu Lys Glu Cys Ala Ile Cys Arg Lys Glu Ile Gln Ala
            370                 375                 380
Asn Val Arg Ala Phe Leu Ser
385                 390

<210> SEQ ID NO 3
<211> LENGTH: 308
<212> TYPE: DNA
<213> ORGANISM: Harmonia axyridis

<400> SEQUENCE: 3
cattgtggta cccgaatgc aattacctt tattgaagaa aaccccagcc tttgtcgaag      60
atattcagaa aaacgaata gctaataaag ttgaaaaaga agaatcacat cataaagaag    120
gagaatcatg taaaaagaa gaagaatctt gtataaagga aaatgagatt gaagcgtgtt    180
gtagctctaa tagtgacacc aaagaaactc ctagcaatcc tatcacaatt gtagaggaga    240
gaaaatctga gaacgtatg ccagtgtgca aaatttgtta tacaaacaat gcggcaattt    300
tgttttg                                                              308

<210> SEQ ID NO 4
<211> LENGTH: 102
<212> TYPE: PRT
<213> ORGANISM: Harmonia axyridis

<400> SEQUENCE: 4

Leu Trp Tyr Pro Glu Cys Asn Tyr Leu Leu Lys Lys Thr Pro Ala
1               5                   10                  15
Phe Val Glu Asp Ile Gln Lys Lys Arg Ile Ala Asn Lys Val Glu Lys
            20                  25                  30
Glu Glu Ser His His Lys Glu Gly Glu Ser Cys Lys Lys Glu Glu
            35                  40                  45
Ser Cys Ile Lys Glu Asn Glu Ile Glu Ala Cys Cys Ser Ser Asn Ser
    50                  55                  60
Asp Thr Lys Glu Thr Pro Ser Asn Pro Ile Thr Ile Val Glu Glu Arg
65                  70                  75                  80
Lys Ser Glu Glu Arg Met Pro Val Cys Lys Ile Cys Tyr Thr Asn Asn
                85                  90                  95
Ala Ala Ile Leu Phe Leu
            100

<210> SEQ ID NO 5
<211> LENGTH: 278
```

<212> TYPE: DNA
<213> ORGANISM: Oxya yezoensis

<400> SEQUENCE: 5

```
ctctgtggtt ttccaagtgt gtgtttgtga ttcttgtgaa gggcaaagat tttgtagata      60
atatctgcca gaacaaagac gcgataatta ctgcgaagga ggcctctaat attaaactgc     120
ctccaaacct tcaggaagct gtcaaagttg ttagcccgga agcagcaagt gcagcatcgt     180
ctgaacagca gttgcctgtt ataagtactg agagggagt cgaagaccct cgcctgtgta      240
aaatttgctt ccaggaagag atgggagtgc tattcctt                             278
```

<210> SEQ ID NO 6
<211> LENGTH: 92
<212> TYPE: PRT
<213> ORGANISM: Oxya yezoensis

<400> SEQUENCE: 6

```
Leu Trp Phe Ser Lys Cys Val Phe Val Ile Leu Val Lys Gly Lys Asp
1               5                   10                  15

Phe Val Asp Asn Ile Cys Gln Asn Lys Asp Ala Ile Ile Thr Ala Lys
            20                  25                  30

Glu Ala Ser Asn Ile Lys Leu Pro Pro Asn Leu Gln Glu Ala Val Lys
        35                  40                  45

Val Val Ser Pro Glu Ala Ala Ser Ala Ala Ser Ser Glu Gln Gln Leu
    50                  55                  60

Pro Val Ile Ser Thr Glu Arg Glu Ile Glu Asp Pro Arg Leu Cys Lys
65                  70                  75                  80

Ile Cys Phe Gln Glu Glu Met Gly Val Leu Phe Leu
                85                  90
```

<210> SEQ ID NO 7
<211> LENGTH: 20
<212> TYPE: DNA
<213> ORGANISM: Artificial Sequence
<220> FEATURE:
<223> OTHER INFORMATION: iap sense primer(iap-01)
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 7

```
gcngangcng gnttytwyta                                                   20
```

<210> SEQ ID NO 8
<211> LENGTH: 22
<212> TYPE: DNA
<213> ORGANISM: Artificial Sequence
<220> FEATURE:
<223> OTHER INFORMATION: iap sense primer(iap-02)
<220> FEATURE:
<221> NAME/KEY: misc_feature
<222> LOCATION: (5)..(5)

```
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine

<400> SEQUENCE: 8
gayknnccnt gggarsarca yg                                         22

<210> SEQ ID NO 9
<211> LENGTH: 23
<212> TYPE: DNA
<213> ORGANISM: Artificial Sequence
<220> FEATURE:
<223> OTHER INFORMATION: iap antisense primer(iap-03)
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 9
cangynryna nrtgnccrca ngg                                        23

<210> SEQ ID NO 10
<211> LENGTH: 25
<212> TYPE: DNA
<213> ORGANISM: Artificial Sequence
<220> FEATURE:
<223> OTHER INFORMATION: primer for 5' RACE(Hv-iap-01)

<400> SEQUENCE: 10
cttcgaccca atctttcaga ccgcc                                      25

<210> SEQ ID NO 11
<211> LENGTH: 25
<212> TYPE: DNA
<213> ORGANISM: Artificial Sequence
<220> FEATURE:
<223> OTHER INFORMATION: primer for 5' RACE(Hv-iap-02)

<400> SEQUENCE: 11
aaagcgcgtg ctgttcccac ggatc                                      25

<210> SEQ ID NO 12
<211> LENGTH: 25
<212> TYPE: DNA
<213> ORGANISM: Artificial Sequence
```

<220> FEATURE:
<223> OTHER INFORMATION: primer for 3' RACE(Hv-iap-03)

<400> SEQUENCE: 12
gatccgtggg aacagcacgc gcttt    25

<210> SEQ ID NO 13
<211> LENGTH: 25
<212> TYPE: DNA
<213> ORGANISM: Artificial Sequence
<220> FEATURE:
<223> OTHER INFORMATION: primer for 3' RACE(Hv-iap-04)

<400> SEQUENCE: 13
gaaacaacgc agaggaaagc tcgac    25

<210> SEQ ID NO 14
<211> LENGTH: 44
<212> TYPE: DNA
<213> ORGANISM: Artificial Sequence
<220> FEATURE:
<223> OTHER INFORMATION: primer for PCR(T7-KS)

<400> SEQUENCE: 14
taatacgact cactataggg agaccactcg aggtcgacgg tatc    44

<210> SEQ ID NO 15
<211> LENGTH: 47
<212> TYPE: DNA
<213> ORGANISM: Artificial Sequence
<220> FEATURE:
<223> OTHER INFORMATION: primer for PCR(T7-SK)

<400> SEQUENCE: 15
taatacgact cactataggg agaccaccgc tctagaacta gtggatc    47

<210> SEQ ID NO 16
<211> LENGTH: 2012
<212> TYPE: DNA
<213> ORGANISM: Henosepilachna vigintioctopunctata

<400> SEQUENCE: 16
ggtaaatgtc atggttatgc aaggaagtaa ccatcccgtg tttatgttta tattactagt    60
tcgtttcaat tactctaaaa tttgtagtgg atataatcaa gataattgtt ctggctttac    120
gatttctgca actcataagt tttaaacctc gcattcgaaa atggttccac cagtagaagt    180
attgtcttat ccaagctcga ctaggaagtt tggtaacgga cttgatttga agaatatgcc    240
cgcagcagta agtgtgaaga gaaatataaa tcataccata ggaaaagaca ctggcgataa    300
tggttgttcc ttttttgaatc taactccacc cgcaaattta ttggctacga tcagggacg    360 cctgaagacg tacaaaaatt ggcccaacaa gaatatagat ccccagaagt tagcggccgc    420 cggcttttc tattctggaa aaactgacat cgtcgagtgt ttcaagtgcg gtatcaaggg    480
acacaactgg ttgttgaacg acgatccaat ggaagatcac aaaaaatgga ataggaattg    540
ttcttttgta agagaaaacg cacccgaaga aaataacgtc ccacaaactg caccggtag    600 tgattattgt ggcaatttag acgtcgtaac ctcacaatat acagtcagcg aagaacctgg    660
agattattat cgtaacttgg gtgtggacat ctctccgttc ttgcaaactg cgctaaaac    720 gaatcagtcc gagggtcata acctggaggg gttgttacta agaacgagga agggcccaag    780
tcacccagat cagatcattt acgagcgtag agtggcgaca ttcgcgaatt ggcccaagtc    840

```
cttgaaacag aaacccacgg acttggcggc cgcaggcttt tactacctcg aatcggcga      900 ccagacgttg tgcttttact gcggcggcgg tctgaaagat tgggtcgaag aagacgatcc     960
gtgggaacag cacgcgcttt ggttcccca gtgtaattat ctattattga agaaaacacc    1020
cgctttcgtc aaagacgtcc aagaaaaaca taaaggcgat tgtcgtcat ccaagcaaaa    1080 cgagaccgaa gtggtagcaa gtagtagcag tagtcacaac tccaaagaat ctccaagtgc    1140
ggtggtagaa gagcgagaaa gaaacaacgc agaggaaagc tcgacattat gcaaaatatg    1200
ttataaaaat gaattggctg ttgtatttct accttgcggt catatggtag cttgtgtaga    1260
ttgtgcatca ggattaaaag aatgtgctat ttgccgtaaa gagatccaag cgaatgttcg    1320
agcctttttg tcatagttcg cgaacagtta acagtaacag ttactgcttg accacactca    1380
ttttcaaaga agtatggtcg aattatgtct ccagctcaaa atcaccacca aacagtgaca    1440
cgttgtggat gcatttgtgt ttcgacaatt acaggtgggt tctcagaacc ctaaaagtgg    1500 cagtttggc gattaacaaa cccatctagg tgaaaatgtg ctgcgtcgct cacgaagatt     1560
ttgctcgaaa tacagcattc cctttgatg ccgtatgttg caaactttct tcactgtgca    1620
tgggcaaaag gcttcagttg ttgtggttat tgaatttggc aagcatgagg acacagatct    1680
ttactgatta tacgctgtag agagcttctt gaaatttgaa attcttgtcc acgacgtcga    1740
attgagattc ctggattgtc actgacactt cgacgtacta ctgtgatttt gacatttgga    1800
cgaccattgt atatgacgta caacggat cctgtctccc tgaattcttc atctcttcac     1860
agttgacgaa gttaaaacac tattccgaca acatttcgaa tgaaatttta gaactgctct    1920
gccaagcttt cattattttt gaatattgt tcaataatga agtaacgttg ttctatcgtg     1980
taatgttcca ttttaataa ccttaaactg tc                                    2012

<210> SEQ ID NO 17
<211> LENGTH: 340
<212> TYPE: DNA
<213> ORGANISM: Helicoverpa armigera

<400> SEQUENCE: 17
caccggtcag ggggataaga ccaagtgttt ctattgcgat ggcggtttga aagactggga      60
aaatgatgac gtgccctggg aacagcacgc gcgctggttc gaccgctgcg cctacgtgca    120
gctggtgaag ggccgcgagt acgtacagaa ggtgatgtcc gaggcctgcg tggtgacggc    180
ggccgaggcg gagaaggacg tggcgccggc ccggccgccc agccagccca ccacacccag    240
cacgcaaccc gaaacgccgg aaaactccgt agacgattcc aaattgtgta aaatctgtta    300
tgcagaggag cgcaacgtgt gcttcgtacc gtgcggacac                           340

<210> SEQ ID NO 18
<211> LENGTH: 113
<212> TYPE: PRT
<213> ORGANISM: Helicoverpa armigera

<400> SEQUENCE: 18

Thr Gly Gln Gly Asp Lys Thr Lys Cys Phe Tyr Cys Asp Gly Gly Leu
1               5                   10                  15

Lys Asp Trp Glu Asn Asp Asp Val Pro Trp Glu Gln His Ala Arg Trp
            20                  25                  30

Phe Asp Arg Cys Ala Tyr Val Gln Leu Val Lys Gly Arg Glu Tyr Val
        35                  40                  45

Gln Lys Val Met Ser Glu Ala Cys Val Val Thr Ala Ala Glu Ala Glu
    50                  55                  60
```

Lys Asp Val Ala Pro Ala Arg Pro Pro Ser Gln Pro Thr Thr Pro Ser
65                  70                  75                  80

Thr Gln Pro Glu Thr Pro Glu Asn Ser Val Asp Asp Ser Lys Leu Cys
                85                  90                  95

Lys Ile Cys Tyr Ala Glu Glu Arg Asn Val Cys Phe Val Pro Cys Gly
            100                 105                 110

His

<210> SEQ ID NO 19
<211> LENGTH: 373
<212> TYPE: DNA
<213> ORGANISM: Blatta lateralis

<400> SEQUENCE: 19
cacaggcaaa ggggatcaga cagtatgttt ccactgcggt ggaggtctca aagactggga      60
ggagaccgat gatccatggg ttgagcatgc agcgtggttc cccaagtgca tccacttagt     120
gctcataaag gacgcgaat tcatagaaaa agtgcaaagt ctgaaagaaa agaaaattcc      180
cgtgcaggaa tacatagatt tgctggagga aggacagaag tcaaaagctt catcatcgtc     240
gtcaagtaca agtacagaga aggaagttga accatcgcag aaagagaagt ccgatgtatc     300
tgaggagaaa gtgatagacg atgcacgact ctgccagata tgttttaccg aggagcgtgg     360
agtgttgttc tta                                                        373

<210> SEQ ID NO 20
<211> LENGTH: 124
<212> TYPE: PRT
<213> ORGANISM: Blatta lateralis

<400> SEQUENCE: 20

Thr Gly Lys Gly Asp Gln Thr Val Cys Phe His Cys Gly Gly Gly Leu
1               5                   10                  15

Lys Asp Trp Glu Glu Thr Asp Asp Pro Trp Val Glu His Ala Ala Trp
                20                  25                  30

Phe Pro Lys Cys Ile His Leu Val Leu Ile Lys Gly Arg Glu Phe Ile
            35                  40                  45

Glu Lys Val Gln Ser Leu Lys Glu Lys Ile Pro Val Gln Glu Tyr
        50                  55                  60

Ile Asp Leu Leu Glu Glu Gly Gln Lys Ser Lys Ala Ser Ser Ser Ser
65                  70                  75                  80

Ser Ser Thr Ser Thr Gly Lys Glu Val Glu Pro Ser Gln Lys Glu Lys
                85                  90                  95

Ser Asp Val Ser Glu Glu Lys Val Ile Asp Asp Ala Arg Leu Cys Gln
            100                 105                 110

Ile Cys Phe Thr Glu Glu Arg Gly Val Leu Phe Leu
        115                 120

<210> SEQ ID NO 21
<211> LENGTH: 23
<212> TYPE: DNA
<213> ORGANISM: Artificial Sequence
<220> FEATURE:
<223> OTHER INFORMATION: iap antisense primer(iap-08)
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature

```
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 21
gcrcayttns crcangcnac nac                                           23

<210> SEQ ID NO 22
<211> LENGTH: 45
<212> TYPE: DNA
<213> ORGANISM: Artificial Sequence
<220> FEATURE:
<223> OTHER INFORMATION: primer for PCR (T7-PCR4R)

<400> SEQUENCE: 22
taatacgact cactataggg agaccaccga attgaattta gcggc                   45

<210> SEQ ID NO 23
<211> LENGTH: 45
<212> TYPE: DNA
<213> ORGANISM: Artificial Sequence
<220> FEATURE:
<223> OTHER INFORMATION: primer for PCR (T7-PCR4L)

<400> SEQUENCE: 23
taatacgact cactataggg agaccacgtc ctgcaggttt aaacg                   45

<210> SEQ ID NO 24
<211> LENGTH: 37
<212> TYPE: DNA
<213> ORGANISM: Artificial Sequence
<220> FEATURE:
<223> OTHER INFORMATION: Hv-iap-NotI- sense primer

<400> SEQUENCE: 24
ataagaatgc ggccgcgcgg aggcggggtt ttattac                            37

<210> SEQ ID NO 25
<211> LENGTH: 36
<212> TYPE: DNA
<213> ORGANISM: Artificial Sequence
<220> FEATURE:
<223> OTHER INFORMATION: Hv-iap-NotI- antisense primer

<400> SEQUENCE: 25
atagtttagc ggccgccagg cgatgagatg gccaca                             36

<210> SEQ ID NO 26
<211> LENGTH: 20
<212> TYPE: DNA
<213> ORGANISM: Artificial Sequence
<220> FEATURE:
<223> OTHER INFORMATION: EF-1a sense primer

<400> SEQUENCE: 26
tgtggaagtt tgagaccacc                                               20

<210> SEQ ID NO 27
<211> LENGTH: 19
<212> TYPE: DNA
```

```
<213> ORGANISM: Artificial Sequence
<220> FEATURE:
<223> OTHER INFORMATION: EF-1a antisense primer

<400> SEQUENCE: 27
gcaagcaatg cgtgctcac                                              19
```

INSECT PEST CONTROL METHOD

TECHNICAL FIELD

The present invention relates to means of insect pest control, and more specifically to a pest control method, a pest control agent to be used in the method and a transgenic plant. The present application claims priority based on Japanese Patent Application No. 2009-136701 filed on Jun. 5, 2009, and the content of the patent application is hereby incorporated by reference herein in its entirety.

BACKGROUND ART

In prior art pest control, chemical pesticides containing organic or inorganic compounds as active ingredients are used. Chemical pesticides are generally poisonous substances, and have low host specificity, so that they are highly toxic to human body and livestock, and markedly affect the environment. In addition, they tend to produce resistant strains. Biotic pesticides were developed as alternatives or supplements to chemical pesticides. Biotic pesticides have many advantages such as little persistence in the environment, low toxicity to human body, high host specificity, and little tendency to produce resistant strains, and thus are expected to expand the range of applications. Biotic pesticides are prepared from, for example, insect bodies, insect extracts, microorganism bodies, microbial extracts, and plant extracts. Recently, biotic pesticides using gene recombination technologies have been developed (for example, see Patent Documents 1 to 3). In addition, as a new approach, the use of RNAi (RNA interference) for pest control has been attempted (for example, see Non-patent Documents 1 to 4).

PRIOR ART DOCUMENTS

[Patent Documents]
  Patent Document 1 Japanese Unexamined Patent Application Publication No. 2002-159230
  Patent Document 2 Japanese Patent No. 3033959
  Patent Document 3 Japanese Patent No. 3532943
[Non-Patent Documents]
  Non-Patent Document 1 Baum, J. A. et al. (2007) Control of coleopteran insect pests through RNA interference. Nat. Biotechnol. 25, 1322-1326
  Non-Patent Document 2 Mao, Y. B. et al. (2007) Silencing a cotton bollworm P450 monooxygenase gene by plant-mediated RNAi impairs larval tolerance of gossypol. Nat. Biotechnol. 25, 1307-131
  Non-Patent Document 3 Price, D. R. G. and Gatehouse J. A. (2008) RNAi-mediated crop protection against insects. Trends in Biotechnology Vol. 26 No. 7, 393-400
  Non-Patent Document 4 Whangbo, J. S. and Hunter C. P. (2008) Environmental RNA interference. Trends in Genetics Vol. 24 No. 6, 297-305

SUMMARY OF THE INVENTION

Problems to be Solved by the Invention

Biotic pesticides have more advantages than chemical pesticides, but generally offer poor versatility. In addition, many biotic pesticides are only effective to specific developmental stages of pests (for example, some are effective to larva or adult only). Furthermore, many biotic pesticides do not have immediate effectivity. In addition, they are said to hardly produce resistant strains, but some of them can produce resistant strains.

Accordingly, the present invention is intended to provide means of pest control which solves many problems with prior art biotic pesticides, and exhibits marked pest control effect.

Means to Solve the Problem

In view of the above-described problems, the inventors focused on inhibitor of apoptosis (IAP) which is indispensable for survival, and devised a strategy including "incorporating an IAP inhibitor into the body of a pest, and inhibiting the IAP thereby achieving pest control effect". Then, in order to validate the efficacy of the strategy, an experiment was carried out using a double strand RNA (dsRNA) which specifically inhibits the IAP expression. As a result of this, as shown by the below-described examples, the IAP inhibition achieved marked pest control effect. The IAP is an indispensable factor for survival, and is constantly expressed in any organisms (regardless of the developmental stage of the organisms). Accordingly, the above-described strategy targeted at the IAP is applicable to any pests in various developmental stages. In other words, the measure offers versatility and is suitable for a wide range of pests. In addition, the targeting at IAP allows achievement of pest control effect with high specificity. Furthermore, the selection of one or more IAPs according to the intended use allows the adjustment of the type (range) of the pests to be controlled. More specifically, the range of pest control is freely established, which cannot be achieved by prior art biotic pesticides.

When an RNA which specifically inhibits the expression of IAP is used as an IAP inhibitor (typically RNAi is used), only specific pests are specifically controlled according to the high level of the specificity. More specifically, very high specificity is exhibited. In addition, when RNAi is used, pest control effect is rapidly achieved, and, owing to its properties, the possibility of occurrence of resistant strains is likely very low. Furthermore, RNAi does not modify plant genes, and thus will not genetically influence them. Therefore, under the above-described strategy, the use of an RNA as an IAP inhibitor will bring many advantages.

The present invention has been accomplished based on the above-described study, and its aspects are as follows.

[1] A pest control method including incorporating an inhibitor against inhibitor of apoptosis (IAP) into the body of a target pest.

[2] The pest control method of [1], wherein the target pest is an agricultural pest, a sanitary pest, or an unpleasant pest.

[3] The pest control method of [1], wherein the target pest is an insect belonging to Coleoptera, Orthoptera, Lepidoptera, or Blattodea.

[4] The pest control method of [1], wherein the target pest is an insect belonging to Coleoptera: Coccinellidae, Orthoptera: Catantopidae, Lepidoptera: Noctuidae, or Blattodea: Blattidae.

[5] The pest control method of [1], wherein the target pest is *Henosepilachna vigintioctopunctata, Harmonia axyridis, Oxya yezoensis, Helicoverpa aimigera*, or *Blatta lateralis*.

[6] The pest control method of any one of [1] to [5], wherein the inhibitor is a compound selected from the group consisting of the following (a) to (d):

(a) an siRNA targeted at a gene coding the inhibitor of apoptosis of the target pest;

(b) a nucleic acid construct intracellularly producing an siRNA targeted at a gene coding the inhibitor of apoptosis of the target insect;

(c) an antisense nucleic acid targeted at the transcript product of a gene coding the inhibitor of apoptosis of the target pest;

(d) a ribozyme targeted at the transcript product of a gene coding the inhibitor of apoptosis of the target pest.

[7] The pest control method of [6], wherein the gene includes the sequence set forth in SEQ ID NO: 1, the sequence set forth in SEQ ID NO: 3, the sequence set forth in SEQ ID NO: 5, the sequence set forth in SEQ ID NO: 16, the sequence set forth in SEQ ID NO: 17, or the sequence set forth in SEQ ID NO: 19.

[8] The pest control method of any one of [1] to [7], including making a plant, which is to be attacked by the target pest, possess an agent containing the inhibitor by application, spraying, or atomization in advance, and incorporating the inhibitor into the body of the target pest by ingestion of the plant,

[9] The pest control method of any one of [1] to [7], including placing a feed containing the inhibitor at the site of occurrence or in the route of entry of the target pest, and incorporating the inhibitor into the body of the target pest by ingestion of the plant.

[10] The pest control method of any one of [1] to [7], including incorporating the inhibitor into the body of the target pest by ingestion of a transgenic plant containing a gene coding the inhibitor.

[11] The pest control method of [10], wherein the inhibitor is a compound selected from the group consisting of the following (A) to (C):

(A) an siRNA targeted at a gene coding the inhibitor of apoptosis of the target pest;

(B) an antisense nucleic acid targeted at the transcript product of a gene coding the inhibitor of apoptosis of the target pest;

(C) a ribozyme targeted at the transcript product of a gene coding the inhibitor of apoptosis of the target pest.

[12] An pest control agent including an inhibitor against inhibitor of apoptosis of the target pest.

[13] The pest control agent of [12], wherein the inhibitor is a compound selected from the group consisting of the following (a) to (d):

(a) an siRNA targeted at a gene coding the inhibitor of apoptosis of the target pest;

(b) a nucleic acid construct intracellularly producing an siRNA targeted at a gene coding the inhibitor of apoptosis of the target insect;

(c) an antisense nucleic acid targeted at the transcript product of a gene coding the inhibitor of apoptosis of the target pest;

(d) a ribozyme targeted at the transcript product of a gene coding the inhibitor of apoptosis of the target pest.

[14] A transgenic plant containing a gene coding the inhibitor against inhibitor of apoptosis of a target pest.

BRIEF DESCRIPTION OF THE DRAWINGS

FIG. 1 summarizes the results of the experiment on *Henosepilachna vigintioctopunctata* as the test insect, describing the change over time in the larvae ingested potato leaves spotted with an RNA (Hv-iap dsRNA) targeted at the IAP gene. Potato leaves spotted with H$_2$O were given to the control group.

FIG. 2 summarizes the results of the experiment on *Henosepilachna vigintioctopunctata* as the test insect, showing the condition of the potato leaves after a lapse of 64 hours from the initiation of ingestion. The upper row shows the result of the test group (the group ingested potato leaves spotted with Hv-iap dsRNA), and the lower row shows the result of the control group.

FIG. 3 summarizes the results of the experiment on *Henosepilachna vigintioctopunctata* as the test insect, showing the comparison of the time elapsed from the initiation of ingestion to death between the test group and the control group. The values are the average of five insects.

FIG. 4 summarizes the results of the experiment on *Helicoverpa armigera* as the test insect, showing the time elapsed from the initiation of ingestion to death. The change with time was observed in the larvae ingested an artificial feed containing an RNA (Har-iap dsRNA) targeted at the IAP gene. The control group ingested an artificial feed containing GFP dsRNA.

FIG. 5 summarizes the results of the experiment on *Blatta lateralis* as the test insect, showing the change with time in the larvae ingested an aqueous solution of Bl-iap dsRNA. The motion (behavior) and survival condition were studied. The control group ingested an aqueous solution of DsRed dsRNA.

FIG. 6 summarizes the result of the experiment on *Henosepilachna vigintioctopunctata* as the test insect, showing the change with time in the larvae of *Henosepilachna vigintioctopunctata* ingested an RNA extracted from *Nicotiana benthamiana* leaves wherein iap (Hv-iap) had been expressed. As the control groups, the positive control group ingested Hv-iap synthetic dsRNA, and the negative control group ingested total RNA extracted from the leave tissues of *N. benthamiana* wherein virus alone had been expressed.

DESCRIPTION OF EMBODIMENT (Insect Pest Control Method)

A first aspect of the present invention relates to a pest control method. The "pests" in the present invention are not particularly limited. In general, pests are broadly divided into agricultural pests, sanitary pests, and unpleasant pests. "Agricultural pests" refer to the pests which attack crops (including garden crops and crops during storage). The pests which attack crops during storage may be referred to as "stored grain pests". "Sanitary pests" refer to the pests which attack the sanitary environment of human. In addition, "unpleasant pests" refer to the pests which attack the mood of human by their appearance or motion. The present invention is also applicable to the pests which attack the assets of human (for example, termite and bristletail) and livestock (for example, mosquito and parasite).

Examples of the classification of pests include Lepidoptera (for example, Plutellidae, Noctuidae, Pyralidae, Tortricidae, Lyonetiidae, Carposinidae, Gelechiidae, Crambidae, Arctiidae, and Lymantriidae), Hemiptera (for example, Cicadellidae, Delphacidae, Psyllidae, Aphididae, Aleyrodidae, Orthezidae, Miridae, Tingidae, Pentatomidae, and Lygaeidae), Coleoptera (for example, Scarabaeidae, Elateridae, Coccinellidae, Cerambycidae, Chrysomelidae, and Curculionidae), Diptera (for example, Muscidae, Calliphoridae, Sarcophagidae, Anthomyiidae, Tephritidae, Opomyzoidea, and Carnoidea), Orthoptera (for example, Acrididae, Catantopidae, and Pyrgomorphidae), Thysanoptera (for example, Thripidae, Aeolothripidae, and Merothripidae), Tylenchida (for example, Aphelenchoididae and Neotylechidae), Collembola (for example, *Onychiurus* and Isotomidae), Acarina (for example, Tetranychidae, Dermanyssidae, Acaridae, and Sarcoptidae), Stylommatophora (for example, Philomycidae and Bradybaenidae), Ascaridida (for example, Ascaridida and Anisakidae), Opisthorchiida, Strigeidida, Blattodea (for example, Blaberidae, Cryptocercidae, and Panesthiidae) and Thysanura (for example, Lepismatidae, Lepidotrichidae, and Nicoletiidae).

Examples of the pests belonging to Lepidoptera include *Chilo suppressalis Walker, Cnaphalocrocis medinalis, Parnara guttata, Sesamia inferens, Mythimna separata, Naranga aenescens Moore, Spodoptera litura, Etiella zinckenella, Etiella behrii, Matsumuraeses falcana, Leguminivora glycinivorella, Pleuroptya naafis, Agrotis segetum, Agrotis ipsilon, Helcystogramma triannulellum, Xestia c-nigrum, Helicoverpa assulta, Helicoverpa armigera, Mamestra brassicae, Spodoptera exigua, Plutella xylostella, Pieris rapae, Pieris brassicae, Hellulla undalis*, and *Autographa nigrisigna*.

Examples of the pests belonging to Hemiptera include *Nilaparvata lugens, Sogatella furcifera, Laodelphax stratella, Nephotettix cincticeps, Recilia dorsalis, Stenotus rubrovittatus, Trigonotylus caelestialium, Leptocorisa chinensis, Nezara antennata, Nezara viridula, Lagynotomus elongatus, Scotinophara lurida, Eysarcoris annamita, Eysarcoris lewisi, Eysarcoris ventralis, Togo hemipterus Scott, Cletus punctiger, Piezodorus hybneri, Halyomorpha halys, Dolycoris baccarum, Neotoxoptera formosana, Rhopalosiphum padi, Rhopalosiphum maidis*, and *Aphis glycines*.

Examples of the pests belonging to Coleoptera include rice *Lissorhoptrus oryzophilus, Oulema oryzae, Echinocnemus squameus, Melanotus legatus, Melanotus fortnumi, Anomala cuprea, Popillia japonica, Maladera castanea, Epilachna varivestis, Paraluperodes nigrobilineatus, Epilachna vigintioctomaculata, Henosepilachna vigintioctopunctata, Harmonia axyridis, Anomala rufocuprea, Anomala testaceipes, Aulacophora indica*, and *Phyllotreta striolata*.

Examples of the pests belonging to Diptera include *Chlorops oryzae, Hydrellia griseola, Sitodiplosis mosellana, Delia platura, Asphondylia yushimai, Melanagromyza sojae, Liriomyza trifolii, Liriomyza sativae, Liriomyza huidobrensis*, and *Liriomyza bryoniae*.

Examples of the pests belonging to Orthoptera include *Oxya yezoensis* and *Oxya japonica*. Examples of the pests belonging to Thysanoptera include *Stenchaetothrips biformis* and *Thrips palmi*. Examples of the pests belonging to Tylenchida include Meloidogyne, Nematoda, and Heterodera. Examples of the pests belonging to Collembola include *Onchiurus psuedamatus yagii* and *Onychiurus matsumotoi*. Examples of the pests belonging to Acarina include *Penthaleus major, Tetranychus urticae, Tetranychus kanzawai, Tyrophagus putrescentiae*, and *Tarsonemus bilobatus*. Examples of the pests belonging to Stylommatophora include Helix and Philomycidae. Examples of the pests belonging to Ascaridida include *Ascaris lumbricoide*. Examples of the pests belonging to Opisthorchiida include *Metagonimus yokogawai*. Examples of the pests belonging to Strigeidida include *Schistosoma japonicum*. Examples of the pests belonging to Blattodea include *Blattella germanica, Periplaneta fuliginosa, Periplaneta americana*, and *Blatta lateralis*. Examples of the pests belonging to Thysanura include Ctenolepisma and Lepisma.

In view of the technical features of the present invention and the technical common knowledge in this field, the coverage of the present invention (more specifically the pests to which the pest control method of the present invention is applicable) is wide. On the other hand, as shown in the below-described examples, the efficacy or effectiveness of the present invention was confirmed by the experiments on *Henosepilachna vigintioctopunctata* and *Harmonia axyridis* belonging to Coleoptera: Coccinellidae, *Oxya yezoensis* belonging to Orthoptera: Catantopidae, *Helicoverpa armigera* belonging to Lepidoptera: Noctuidae, and *Blatta lateralis* belonging to Blattodea: Blattidae as test insects. In consideration of the fact, though there is no intention to limit the coverage of the present invention, the present invention is preferably applied to the insects belonging to Coleoptera, Orthoptera, Lepidoptera, or Blattodea, and more preferably to the insects belonging to Coleoptera: Coccinellidae, Orthoptera: Catantopidae, Lepidoptera: Noctuidae, or Blattodea: Blattidae. Specific examples of the insects belonging to Coleoptera: Coccinellidae include *Henosepilachna vigintioctopunctata* and *Harmonia axyridis*, and specific examples of the insects belonging to Orthoptera: Catantopidae include *Oxya yezoensis*. Specific examples of the insects belonging to Lepidoptera: Noctuidae include *Helicoverpa armigera*, and specific examples of the insects belonging to Blattodea: Blattidae include *Blatta lateralis*.

In the present description, "pest control" refers to the removal or the reduction of harm of pests. The concept of "pest control" include killing of pests (extermination), pest proliferation inhibition, pest growth inhibition, repelling of pests (repellence), and the removal or the reduction of harm of pests (for example, inhibition of ingestion capacity of agricultural pests.

According to the pest control method of the present invention, an inhibitor (IAP inhibitor) against inhibitor of apoptosis (hereinafter abbreviated as "IAP") is incorporated into the body of the target pest. The term "IAP inhibitor" is used as the generic name of the substances inhibiting IAP, The IAP inhibitor may be of any type as long as it has inhibitory activity against IAP.

The "target pest" refers to the pest subjected to pest control, or the pest controlled by the present invention. The target pest may be two or more pests.

In the present invention, an IAP inhibitor corresponding to the target pest is used. More specifically, the substance which inhibits the IAP expressed in the body of the target pest is used as "IAP inhibitor". When an IAP inhibitor corresponding to two or more pests is used, or two or more IAP inhibitors are used in combination, two or more pests can be controlled.

Examples of the IAP inhibitor include a nucleic acid which inhibits the expression of the IAP gene, and a substance which specifically binds to IAP (for example, an antibody or a low molecular weight compound). The former one is further described below. The substance which specifically binds to IAP may be obtained or prepared using binding assay targeted at IAP. An antibody which specifically binds to IAP may be prepared using, for example, an immunological method, a phage display method, or a ribosome display method.

According to one aspect of the present invention, a compound selected from the group consisting of the following (a) to (d) is used as the IAP inhibitor:

(a) an siRNA targeted at a gene coding the inhibitor of apoptosis of the target pest;

(b) a nucleic acid construct intracellularly producing an siRNA targeted at a gene coding the inhibitor of apoptosis of the target insect;

(c) an antisense nucleic acid targeted at the transcript product of a gene coding the inhibitor of apoptosis of the target pest;

(d) a ribozyme targeted at the transcript product of a gene coding the inhibitor of apoptosis of the target pest.

The (a) and (b) are the compounds used for the inhibition of expression by so-called RNAi (RNA interference). In other words, when the compound (a) or (b) is used, the expression of IAP is inhibited by RNAi, whereby pest control effect is achieved. In this manner, the use of RNAi allows specific control of the target pest, and facilitates rapid achievement of pest control effect. Furthermore, owing to its properties, the possibility of occurrence of resistant strains is likely extremely low. In addition, RNAi does not modify plant genes, and thus will not genetically influence them.

The "RNAi" refers to the inhibition of expression of the target gene by the introduction of an RNA composed of a sequence homologous to that of the target gene (specifically homologue to the mRNA corresponding to the target gene) into the target cell. For the inhibition of expression using the RNAi method in pests such as insects, generally, a dsRNA (double strand RNA) composed of a sequence corresponding a part of the target gene (the gene coding the IAP of the target pest). Two or more dsRNAs may be used for one target gene.

The RNAi targeted at the gene of a mammal cell uses a short dsRNA (siRNA) of about 21 to 23 nucleotides. When the RNAi is targeted at the gene of a pest such as an insect, a long dsRNA of more than several hundreds of nucleotides is preferred because owing to its effectiveness. The length of the dsRNA used for RNAi is, for example, 30 nucleotides or more, and preferably 200 nucleotides or more (for example, from 200 to 500 nucleotides). The use of a dsRNA is preferred for inducing effective inhibition of expression, but the use of a single strand RNA will also be contemplated. The dsRNA used herein is not necessarily composed of two molecules of sense and antisense strands, and, for example, may have a structure wherein the sense and antisense strands composing the dsRNA are connected via a hairpin loop. A dsRNA composed of a modified RNA may be used. Examples of the modification include phosphorothioation, and the use of a modified base (for example, fluorescence-labeled base).

An RNAi specific to the target gene can be also produced by intracellularly expression of a dsRNA targeted at the target gene. The nucleic acid construct (b) is used as such a means.

The dsRNA used in the RNAi method may be prepared by chemical synthesis, or in vitro or in vivo using an appropriate expression vector. The method using an expression vector is particularly effective for the preparation of a relatively long dsRNA. The design of dsRNA normally includes the sequence (continuous sequence) specific to the target nucleic acid. Programs and algorithms for selecting an appropriate target sequence have been developed.

The above-described Non-patent Documents 1 to 4 (Baum, J. A. et al. (2007) Control of coleopteran insect pests through RNA interference. Nat. Biotechnol. 25, 1322-1326; Mao, Y. B. et al. (2007) Silencing a cotton bollworm P450; monooxygenase gene by plant-mediated RNAi impairs larval tolerance of gossypol. Nat. Biotechnol. 25, 1307-131; Price, D. R. G. and Gatehouse J. A. (2008) RNAi-mediated crop protection against insects. Trends in Biotechnology Vol. 26 No. 7, 393-400; Whangbo, J. S. and Hunter C. P. (2008) Environmental RNA interference. Trends in Genetics Vol. 24 No. 6, 297-305) report the pest control using RNAi, and are used as reference for the implementation of the present invention. Therefore, these documents are hereby incorporated by reference herein in their entirety.

The above-described (c) is a compound used for the inhibition of expression by an antisense method. The inhibition of expression using an antisense method is generally carried out using an antisense construct which produces an RNA complementary to the portion specific to the mRNA corresponding to the target gene upon transcription. The antisense construct (also referred to as antisense nucleic acid) is, for example, introduced into the target cell in the form of an expression plasmid. The antisense construct may be an oligonucleotide probe which hybridizes with the DNA sequence or corresponding mRNA sequence of the target gene (these sequences may be collectively referred to as "target nucleic acid") upon introduction into the target cell, and inhibits their expression. The oligonucleotide probe is preferably resistant to endogenous nucleases such as exonuclease and/or endonuclease. When a DNA molecule is used as an antisense nucleic acid, the DNA molecule is preferably an oligodeoxyribonucleotide derived from the region containing the translation initiation site of the mRNA corresponding to the target gene (for example, the region from −10 to +10).

The complementation between the antisense nucleic acid and target nucleic acid is preferably precise, but some mismatch may occur. The hybridization capacity of the antisense nucleic acid for the target nucleic acid generally depends on the degree of complementation between the nucleic acids and the length of the antisense nucleic acid. In principle, the longer the antisense nucleic acid, the more stable double strand (or triplex) is formed between the antisense and target nucleic acids, even if many mismatches occur. Those skilled in the art can examine the degree of acceptable mismatch using a standard method.

The antisense nucleic acid may be DNA, RNA, or a chimera mixture thereof, or a derivative or modified product thereof. The antisense nucleic acid may be single or double strand. The stability and hybridization capacity of the antisense nucleic acid are improved by the modification of the base, sugar, or phosphoric acid backbone. The antisense nucleic acid may be synthesized by an ordinary method using, for example, a commercially available automatic DNA synthesizing apparatus (for example, manufactured by Applied Biosystems). The preparation of the modified nucleic acid and derivatives may refer to, for example, Stein et al. (1988), Nucl. Acids Res. 16:3209 or Sarin et al., (1988), Proc. Natl. Acad. Sci. U.S.A. 85:7448-7451.

In order to improve the action of the antisense nucleic acid in the target cell, a promoter (for example, actin promoter or ie1 promoter) which strongly acts in the target cell may be used. More specifically, when a construct containing the antisense nucleic acid under control of the promoter is introduced into the target cell, a sufficient amount of antisense nucleic acid is transcribed.

According to one aspect of the present invention, the inhibition of expression by ribozyme is used (when the compound (d) is used). The mRNA corresponding to the target gene may be destroyed using a ribozyme which cleaves the mRNA at the site-specific recognition sequence, but preferably a hammerhead ribozyme is used. The method for constructing the hammerhead ribozyme may be referred to, for example, Haseloff and Gerlach, 1988, Nature, 334:585-591.

In the same manner as in the antisense method, for example, for the purpose of improving stability and target performance, the ribozyme construction may use a modified oligonucleotide. In order to produce an effective amount of ribozyme within the target cell, it is preferred that a nucleic acid construct including DNA coding the ribozyme be used under the control of a promoter which strongly acts in insect cells (for example, an actin promoter or an ie1 promoter).

Specific examples of the sequence of the target gene when any one of the compounds (a) to (d) is used are set forth in SEQ ID NOs: 1, 3, 5, 16, 17, and 19. SEQ ID NO: 1 is the sequence of the IAP gene (partial cDNA) of *Henosepilachna vigintioctopunctata*. SEQ ID NO: 16 is the full length cDNA sequence of the same gene. The amino acid sequence coded by the sequence is set forth in SEQ ID NO: 2. SEQ ID NO: 3 is the sequence of the IAP gene (partial cDNA) of *Harmonia axyridis*. The amino acid sequence coded by the sequence is set forth in SEQ ID NO: 4. SEQ ID NO: 5 is the sequence of the IAP gene (partial cDNA) of *Oxya yezoensis*. The amino acid sequence coded by the sequence is set forth in SEQ ID NO: 6. SEQ ID NO: 17 is the sequence of the IAP gene (partial cDNA) of *Helicoverpa armigera*. The amino acid sequence coded by the sequence is set forth in SEQ ID NO: 18. SEQ ID NO: 19 is the sequence of the IAP gene (partial cDNA) of *Blatta lateralis*. The amino acid sequence coded by the sequence is set forth in SEQ ID NO: 20.

(Incorporation of IAP Inhibitor)

The manner for incorporation of the IAP inhibitor is not particularly limited, and may be selected according to the target pest. When the target pest is a pest which attacks a plant, for example, the agent (pesticide) containing the IAP inhibitor is in advance retained in the plant, which is to be attacked by the target pest, through application, spraying, or atomization. As a result of this, when the target pest ingests the plant, the IAP inhibitor is incorporated into the body of the target pest. On the other hand, when a feed (feed agent) containing the IAP inhibitor is placed at the site of occurrence or in the route of entry of the target pest, the target pest ingests the feed, and thus the IAP inhibitor is incorporated into the body of the target pest. In addition, when the plant to be attacked is modified by the introduction of a gene coding the IAP inhibitor, the IAP inhibitor is incorporated into the body of the target pest when the pest ingests the transgenic plant. The transgenic plant used in this method may be a plant subjected to gene modification so as to express: (A) an siRNA targeted at a gene coding the IAP of the target pest; (B) an antisense nucleic acid targeted at the transcript product of a gene coding the IAP of the target pest; or (C) a ribozyme targeted at the transcript product of a gene coding the IAP of the target pest.

(Insect Pest Control Agent)

A second aspect of the present invention relates to a pest control agent useful in the pest control method. The pest control agent of the present invention is provided in the form of, for example, a pesticide or feed. The pest control agent of the present invention contains an inhibitor (IAP inhibitor) against the IAP of the target pest. Examples of the IAP inhibitor are the following (a) to (d). Details about these compounds are as described above.

(a) an siRNA targeted at a gene coding the IAP of the target pest;

(b) a nucleic acid construct intracellularly producing an siRNA targeted at a gene coding the IAP of the target insect;

(c) an antisense nucleic acid targeted at the transcript product of a gene coding the IAP of the target pest;

(d) a ribozyme targeted at the transcript product of a gene coding the IAP of the target pest.

The form of the pesticide of the present invention is not particularly limited. For example, the pesticide is prepared into a solid, liquid, or gel. Specific examples of the dosage form include powder agents, pellets, wettable powder, water soluble powder, emulsions, solutions, olea, aerosols, microcapsule agents, paste agents, smoking agents, fumigants, and coating agents.

The content of the active ingredient in the pesticide of the present invention depends on the form of the pesticide, and may be, for example, from 0.1% by weight to 50% by weight.

The pesticide of the present invention contains an IAP inhibitor as an active ingredient, and may further contain one or more other active ingredients. Examples of other active ingredients include insecticides (organophosphorus compounds, carbamate agents, synthetic pyrethroid agents, nereistoxin agents, neonicotinoid agents, GABA inhibitors, GABA analogues, respiratory inhibitors, IGR agents (insect growth inhibitors), BT agents), repellents, and attractants. Examples of the other components (additives) which may be contained in the pesticide of the present invention besides the active ingredient include surfactants (anionic surfactants, cationic surfactants, ampholytic surfactants, and nonionic surfactants), thickeners, fluidizers, binders, stickers, spreaders, wetting agents, extenders, carriers, stabilizers, pH controlling agents, anticaking agents, antiseptics, antifreezing agents, antioxidants, ultraviolet absorbers, ultraviolet scattering agents, dispersants, coloring agents, and perfumes.

(Transgenic Plant)

Another aspect (third aspect) of the present invention relates to a transgenic plant. A gene coding the inhibitor against the IAP of the target pest has been introduced into the transgenic plant of the present invention. Typically, the transgenic plant of the present invention has been subjected to gene modification so as to express: (A) an siRNA targeted at a gene coding the IAP of the target pest; (B) an antisense nucleic acid targeted at the transcript product of a gene coding the IAP of the target pest; or (C) a ribozyme targeted at the transcript product of a gene coding the IAP of the target pest.

The transgenic plant of the present invention may be prepared by introducing a gene construct (for example, recombinant vector) containing the desired gene (gene coding the above-described siRNA, antisense nucleic acid, or ribozyme) into the plant body or plant cell. The recombinant vector as the gene construct may be constructed by inserting the desired gene into an appropriate vector. The vector used herein is preferably, for example, a pBI, pPZP, or pSMA vector. The use of these vectors allows gene introduction using *Agrobacterium*. In particular, a pBI binary vector or a medium vector (for example, pBI121, pBI101, pBI101.2, or pBI101.3) is preferred. The binary vector is a shuttle vector duplicable in *Escherichia* coli and *Agrobacterium*. Examples of other vectors useful herein include pUC vectors. The use of a pUC vector allows direct introduction of the desired gene into the plant. Examples of the pUC vector include pUC18, pUC19, and pUC9. Alternatively, a plant virus vector (for example, cauliflower mosaic virus, bean common mosaic virus, or tobacco mosaic virus) may be used.

A recombinant vector is constructed by inserting a purified DNA (containing the desired gene) into the cloning site of the vector. Normally, the desired gene is linked to the sequence (for example, promoter, enhancer, or terminator) necessary for its expression. Other sequences useful for the expression of the desired gene at a high level, for example, the intron sequence or the sequence of 5'-untranslated region of a specific gene may be linked. In addition, the recombinant vector preferably contains a selection marker gene.

The promoter may be a constitutive promoter or a promoter which functions under specific conditions (tissue-specific promoter, growth stage-specific promoter, or inductive promoter), and may be selected according to the intended use. In addition, the origin of the promoter is not particularly limited. Specific examples of the promoter include ubiquitin promoter, califlower mosaic virus 35S promoter, actin promoter, and nopaline synthase gene promoter.

The enhancer is used for increasing the expression efficiency of the desired gene. An example of the enhancer is the enhancer region containing the upstream sequence in the CaMV35S promoter. The terminator is the sequence which terminates the transcript of the gene. Examples of the terminator used herein include CaMV 35S RNA gene terminator, nopaline synthase gene terminator, and octopine synthase gene.

Examples of the selection marker gene include ampicillin resistant gene, neomycin resistant gene, hygromycin resistant gene, β-glucuronidase gene, and luciferase gene.

The method for introducing the desired gene into the plant is not particularly limited. For example, the *Agrobacterium* method, electroporation method, particle gun method, or polyethylene glycol (PEG) method may be used. Among them, the *Agrobacterium* method is particularly preferred. According to the *Agrobacterium* method, the desired gene can be introduced into a protoplast, a tissue piece, or a plant body (in planta method). When a protoplast is used, the desired gene is introduced by cocultivation with *Agrobacterium* having a Ti plasmid, or fusion with *Agrobacterium* spheroplasts (spheroplast method). In addition, when a tissue piece is used, the desired gene is introduced by infection of an aseptically cultured leaf disk or callus. When a plant body is used (in planta method), the desired gene is introduced by direct treatment of, for example, a moistened seed, infant plant (seedling), or potted plant with *Agrobacterium*.

The particle gun method is also a preferable introduction method. When the particle gun method is used, for example, the sample (for example, plant body, plant organ, plant tissue, or protoplast) is treated with gene introduction apparatus (for example, BIOLISTIC POS 1000/He; BioRad). The treatment conditions vary with the sample, but generally the pressure is about 1000 to 1100 psi, and the distance is about 5 to 10 cm. It is preferred that a recombinant vector containing the desired gene and another recombinant vector containing a selection marker gene be mixed, at the same time these two recombinant vectors be shot into the sample (cotransformation).

Whether the desired gene is incorporated into the plant body or not may be confirmed by, for example, the PCR method, southern hybridization method, Northern hybridization method, or Western blotting method. The incorporation of the desired gene may be confirmed using a reporter-gene (for example, beta glucuronidase (GUS), luciferase (LUC), Green fluorescent protein (GFP), chloramphenicol acetyl-transcriptase (CAT), or beta galactosidase (LacZ).

The type of the plant to be transformed is not particularly limited, and examples of the plant include valuable crops such as grains, vegetables, and fruit trees, and ornamental plants such as house plants. In addition, the plant may be a mono-cotyledonous or dicotyledonous plant. Examples of the monocotyledonous plant include the plants belonging to Gramineae (for example, rice, barley, wheat, corn, sugarcane, zoysia, sorghum, foxtail millet, and Japanese millet), Liliaceae (for example, asparagus, lily, onion, Chinese chive, and dogtooth violet), and Zingiberaceae (for example, ginger, mioga, and turmeric). Examples of the dicotyledonous plant include the plants belonging to Brassicaceae (for example, thale-cress, cabbage, rapeseed, cauliflower, broccoli, and Japanese white radish), Solanaceae (for example, tomato, eggplant, potato, and tobacco), Fabaceae (for example, soybean, pea, bean, and alfalfa), Fabaceae (for example, cucumber, melon, and pumpkin), Umbelliferae (for example, carrot, celery, and Japanese hornwort), Asteraceae (for example, lettuce), Malvaceae (for example, cotton plant and okra), Chenopodiaceae (for example, sugar beet and spinach), Myrtaceae (for example, eucalyptus and clove), and Salicaceae (for example, poplar).

The term "plant" includes the plant body, plant organs (for example, leaves, petals, stem, root, rhizome, and seeds), plant tissues (for example, epidermis, phloem, parenchyma, xylem, and vascular bundle), and plant cells. In addition, the term "plant cell" includes seed suspension cultures, embryos, meristematic tissue regions, callus tissues, cells derived from leaves and roots, and gametophytes (embryos and pollens) and their precursors. When plant culture cells are transformed, an organ or individual is regenerated from the transformed cells by a known tissue culture method. These operations are readily performed by those skilled in the art. An example is described below. Firstly, the transformed plant cells are cultured in a sterilized callus forming medium (containing a carbon source, saccharides, vitamins, inorganics, and phytohormones such as auxin and cytokinin), thereby forming a dedifferentiated calluse which indefinitely proliferates (callus induction). The formed callus is transferred to a new medium containing a plant growth regulator such as auxin, and further proliferated thereon (subcultivation). When the callus induction is carried out on a solid medium such as agar and subcultivation is carried out in a liquid medium, the respective cultures are efficiently achieved. Secondly, the callus proliferated by subcultivation was cultured under appropriate conditions, thereby inducing redifferentiation of the organ (inductive redifferentiation), and regenerating the plant body. The inductive redifferentiation is achieved by appropriately adjusting the type and amount of the various components of the medium, including plant growth regulators such as auxin and cytokinin, and the carbon source, and the light and temperature. The inductive redifferentiation forms adventitious embryos, adventitious roots, adventitious buds, adventitious foliage, and others, and they are grown into a complete plant body. The plant before being a complete plant body may be stored in the form of, for example, capsulated artificial seeds, dry embryos, lyophilized cells, or tissues.

The transgenic plant of the present invention prepared as described above produces an inhibitor against the IAP of the target pest upon expression of the introduced desired gene. When the target pest ingests the transgenic plant of the present invention, the IAP inhibitor is incorporated into the body of the target pest, and pest control effect is achieved. The term "transgenic plant" in the present invention includes "T2 generation plant" prepared by transformation treatment, "T2 generation plant" derived from the seeds of the T1 generation plant, and the subsequent generation plants (for example, T3 generation and T4 generation plants).

The above-described Non-patent Documents 1 and 2 (Baum, J. A. et al. (2007) Control of coleopteran insect pests through RNA interference. Nat. Biotechnol. 25, 1322-1326; Mao, Y. B. et al. (2007) Silencing a cotton bollworm P450 monooxygenase gene by plant-mediated RNAi impairs larval tolerance of gossypol. Nat. Biotechnol. 25, 1307-131) report the examples of recombination plants wherein a dsRNA against a specific target is forcedly expressed. As demonstrated by these reports, it is a promising pest control measure to express a dsRNA against the target in a plant body, thereby causing inhibitory effect by the RNAi. Therefore, in the present invention, it is preferred that gene manipulation be carried out such that a dsRNA against the IAP of the target pest is forcedly expressed. In other words, in a preferred embodiment of the transgenic plant of the present invention, as a result of gene manipulation, a dsRNA against the IAP of the target pest is forcedly expressed in the plant body. The above-described two documents are helpful in preparing the transgenic plant of the present invention, so that these documents are hereby incorporated by reference herein in their entirety.

EXAMPLES

A. Study of Pest Control Effect 1

Focusing attention on inhibitor of apoptosis (IAP), the pest control effect by a double strand RNA (dsRNA) which specifically inhibits the expression of IAP was studied.

<Material and Method>

1. Cloning of cDNA Homologue to Inhibitor of Apoptosis and Determination of Base Sequence (1) Test Insects The individuals of *Henosepilachna vigintioctopunctata* were bred from those collected on the leaves of potato in the field of Graduate School of Bioagricultural Sciences and School of Agricultural Sciences, Nagoya University, and the individuals of *Harmonia axyridis* were bred in the laboratory of Graduate School of Bioagricultural Sciences and School of Agricultural Sciences, Nagoya University, and the larvae of *Oxya yezoensis* were collected in a paddy field of Graduate School of Bioagricultural Sciences and School of Agricultural Sciences, Nagoya University.

(2) Preparation of cDNA

Total RNA was extracted from the wing disc of prepupae of *Henosepilachna vigintioctopunctata* (Hv), embryos of *Harmonia axyridis* (Ha), and hindlimb of larvae of *Oxya yezoensis* (Oy), by the hydrochloric acid guanidine method using TRIZOL (LIFE TECHNOLOGIES). Using the RNA as the template, single strand cDNAs for the 5' Rapid amplification of cDNA ends(RACE) and 3' RACE were synthesized using Superscript II reverse transcriptase (GIBCO BRL) based on SMART™ RACE cDNA Amplification Kit (CLONTECH).

(3) RT-PCR

Polymerase chain reaction (PCR) was carried out using the single strand cDNA prepared above used as a template. The Taq DNA polymerase for the PCR was Ampli Taq Gold (PERKIN ELMER). The primers used for the PCR are shown below.

```
(iap sense primer)
                                          (SEQ ID NO: 7)
iap-01: 5'-GCIGAIGCIGGITTYTWYTA-3' (20 mer)

(SEQ ID NO: 8)
iap-02: 5'-GAYKIICCITGGGARSARCAYG-3' (22 mer)

(iap antisense primer)
                                          (SEQ ID NO: 9)
iap-03: 5'-CAIGYIRYIAIRTGICCRCAIGG-3' (23 mer)
``` wherein W represents A+T, S represents C+G, Y represents C+T, R represents A+G, K represents T+G, and I represents inosine.

The combinations of the sense primer and antisense primer and reaction conditions appropriate to the respective species are shown below. iap cDNA

TABLE 1

| Sample | Primer | Number of cycles | Annealing temperature (° C.) | Extension time (minutes) |
|---|---|---|---|---|
| Hv | 01-03 | 50 | 45 | 0.5 |
| Hv | 02-03 | 50 | 45 | 0.5 |
| Ha | 02-03 | 50 | 45 | 0.5 |
| Oy | 02-03 | 50 | 45 | 0.5 |

(4) 5' RACE and 3' RACE

RACE was carried out using the single strand cDNA prepared above as a template, based on the protocol of SMART™ RACE cDNA Amplification Kit (CLONTECH). Based on the partial sequence of the cDNA homologue to the iap of *Henosepilachna vigintioctopunctata*, two primers were designed for each of 5' RACE and 3' RACE. The designed primers are shown below.

```
(For 5' RACE)
                                          (SEQ ID NO: 10)
Hv-iap-01: 5'-CTTCGACCCAATCTTTCAGACCGCC-3' (25 mer)

(SEQ ID NO: 11)
Hv-iap-02: 5'-AAAGCGCGTGCTGTTCCCACGGATC-3' (25 mer)

(For 3' RACE)
                                          (SEQ ID NO: 12)
Hv-iap-03: 5'-GATCCGTGGGAACAGCACGCGCTTT-3' (25 mer)

(SEQ ID NO: 13)
Hv-iap-04: 5'-GAAACAACGCAGAGGAAAGCTCGAC-3' (25 mer)
```

The PCR conditions in the first RACE were as follows: denaturation (94° C., 5 seconds); extension (72° C., 3 minutes) were carried out five cycles, denaturation (94° C., 5 seconds); annealing (70° C., 10 seconds); and extension (72° C., 3 minutes) were carried out five cycles, and then denaturation (94° C., 5 seconds); annealing (68° C., 10 seconds); extension (72° C., 3 minutes) were carried out carried out 25 cycles. The PCR conditions in the second RACE were as follows: denaturation (94° C., 5 seconds); extension (72° C., 3 minutes) were carried out five cycles, denaturation (94° C., 5 seconds); annealing (70° C., 10 seconds); extension (72° C., 3 minutes) were carried out five cycles, and then denaturation (94° C., 5 seconds); annealing (68° C., 10 seconds); extension (72° C., 3 minutes) were carried out 25 cycles, and finally extension reaction was carried out at 72° C. for 10 minutes.

(5) Purification of PCR Product

After completion of the PCR, agarose (Agarose II [DOJINDO]) was added to TBE (89 mM Tris, 89 mM boric acid, 2 mM EDTA), and the PCR product was isolated by electrophoresis in 1% Agarose Ilagarose gel containing 0.5 mg/ml ethidium bromide. The band containing the intended PCR product was cut out, and the PCR product was collected by Mag Extractor (Toyobo) and used as the insert for subcloning.

(6) Subcloning of PCR Product into pBluescript

The insert prepared above was inserted into the Eco RV recognition site of pBluescriptTMKS(+) (pBS). The ligation reaction was carried out using DNA Ligation Kit Ver. 2 (TaKaRa). The ligation reaction solution was used for the transformation into *Escherichia coli* (XL1-Blue). The transformed *Escherichia coli* culture solution was spread over an LB plate, and cultured at 37° C. overnight. White colonies were selected, and the clone with an insertion of the intended PCR fragment was selected using the PCR method. The Taq DNA polymerase for the PCR was Ampli Taq Gold (PERKIN ELMER), and the primers were SK primer and KS primer. The PCR was carried out 25 cycles under conditions that denaturation (95° C., 30 seconds); annealing (55° C., 30 seconds); and extension (72° C., 30 seconds). The selected clone was cultured under shaking in an LB medium at 37° C. overnight, and a plasmid DNA was prepared using FlexiPrep Kit (Amerciam Pharmacia Biotech) according to the protocol of the kit.

(7) Sequencing

The sequence was determined using BigDye Terminator v3.1 Cycle Sequencing kit according to the protocol. The determined sequence was analyzed by DNASIS.

2. RNAi method (1) Amplification of Template for RNA Synthesis

The iap of *Henosepilachna vigintioctopunctata* was prepared by subcloning the RT-PCR product amplified with the iap1 and iap3 primers into the EcoRV site of pBluescript KS+vector (Stratagene). The iap of *Harmonia axyridis* and the iap of *Oxya yezoensis* were prepared by subcloning the RT-PCR product amplified with the iap2 and iap3 primers in the same manner as above.

In order to obtain the PCR product to be used as the template for synthesizing a double strand RNA, the following PCR primers containing the T7 RNA polymerase promoter sequence were used, so as to be useful for any of the genes cloned into the above-described vector.

(T7-KSprimer)
(SEQ ID NO: 14)
5'-TAATACGACTCACTATAGGGAGACCACTCGAGGTCGACGGTATC-3'

(T7-SKprimer)
(SEQ ID NO: 15)
5'-TAATACGACTCACTATAGGGAGACCACCGCTCTAGAACTAGTGGAT
C-3'

The PCR was carried out under the following conditions. In order to obtain a sufficient amount of PCR product, 4 to 8 pieces of the following reaction tube were provided.

| (Reaction solution) | |
|---|---|
| Template DNA (20 to 50 ng) + H₂O | 37.75 μl |
| 10 × buffer | 5 μl |
| 2 mM dNTP | 5 μl |
| 10 pmol/μl T7-KS primer | 1 μl |
| 10 pmol/μl T7-SK primer | 1 μl |
| AmpliTaq Gold (Perkin Elmer) | 0.25 μl |
| Total | 50 μl |

(Temperature Cycle)

[95° C. for 9 minutes]→[94° C. for 60 seconds→55° C. for 30 seconds→72° C. for 30 seconds]×40 cycles→72° C. for 7 minutes→12° C. for ∞

The PCR product obtained by the above reaction was concentrated by ethanol precipitation, and then subjected to agarose electrophoresis, and purified from the gel using Mag Extractor (Toyobo).

(2) Synthesis of Double Strand RNA

RNA was synthesized using 1 μg of the above-described template DNA according to MEGA script T7 Kit (Ambion), and dissolved in an adequate amount of ultrapure water free of nuclease.

In order to anneal the double strand RNA, the RNA solution thus obtained was incubated at 65° C. for 30 minutes using a heating block, and returned to room temperature over a period of 1 to 2 hours.

A small amount of the double strand RNA was subjected to concentration determination and agarose electrophoresis.

After confirmation of the synthesis, the double strand RNA was adjusted to a concentration of 2 μg/μl, divided into individual batches, and stored at −80° C.

(3) Ingestion of Double Strand RNA

The experiment on *Henosepilachna vigintioctopunctata* used third instar larvae. 5 μl of Hv-iap dsRNA were spotted at about 10 places on potato leaves. The potato leaves were given to the larvae, and all the places spotted with the RNA solution were ingested. Water was given to the control group. Thereafter, the larvae were observed over time.

The experiment on *Harmonia axyridis* used male adults two days after emergence. A mixture of 10 mg of an artificial feed composed mainly of drone honeybee powder and sugar and 5 μl of Ha-iap dsRNA was given, Gfp dsRNA was given to the control group in the same manner. Thereafter, the adults were observed over time.

The experiment on *Oxya yezoensis* used adults. After spotting 5 μl of Oy-iap dsRNA in about five places on rice leaves, and then the leaves were given. Gfp dsRNA was given to the control group in the same manner. Thereafter, the adults were observed over time.

<Results>

1. *Henosepilachna vigintioctopunctata* (Coleoptera, Coccinellidae)

FIG. 1 shows the change over time of the larvae (test group) ingested the potato leaves spotted with Hv-iap dsRNA. In comparison with the control group, the amount of ingestion and the quantity of motion decreased in the early stage after the initiation of ingestion. The observation of the potato leaves after a lapse of 64 hours from the initiation of ingestion (FIG. 2) showed that the amount of ingestion was markedly different from that of the test group (upper row) and control group (lower row). In addition, all the larvae of the test group died within 4 days, while all the larvae of the control group were living after a lapse of 4 days (FIG. 3). As described above, the inhibition of IAP through the incorporation of Hv-iap dsRNA into the body rapidly caused ingestion disorder, and inhibited survival and growth. These results indicate that the inhibition of IAP achieves rapid and marked pest control effect.

2. *Harmonia axyridis* (Coleoptera: Coccinellidae)

The Ha-iap dsRNA and gfp dsRNA were each given to two male adults. All the individuals ingested the Ha-iap dsRNA showed a marked decrease in the amount of ingestion within 24 hours. The amount of ingestion for 4.5 days was 10 mg or less in all the individuals ingested the Ha-iap dsRNA, while 20 mg in all the individuals ingested the gfp dsRNA. The individuals ingested the Ha-iap dsRNA died on days 7.5 and 9. On the other hand, all the individuals ingested the gfp dsRNA were living after a lapse of 33 days. These results indicate that the inhibition of IAP achieves marked pest control effect also in *Harmonia axyridis*.

3. *Oxya yezoensis* (Orthoptera: Catantopidae)

The Oy-iap dsRNA and gfp dsRNA were each given to two male adults. As a result of this, all the individuals ingested the Oy-iap dsRNA died on days 9 and 12. On the other hand, all the individuals ingested the gfp dsRNA were living after a lapse of 25 days. These results indicate that the inhibition of IAP achieves marked pest control effect also in *Oxya yezoensis*. The amount of ingestion of rice leaves after ingestion of the dsRNA was not studied because its measurement was difficult.

These result indicate that the incorporation of the IAP inhibitor into the body of pests is a markedly effective control strategy against pests, and that the application range is extensive.

B. Study of Pest Control Effect 2

The efficacy of the pest control strategy targeted at IAP was studied using other insects.

<Material and Method>

1. Cloning of cDNA Homologue to IPA and Sequencing (1) Test Insects

*Helicoverpa armigera, Blatta lateralis* (also referred to as Red Roach or Turkistan Roach) and *Henosepilachna vigintioctopunctata* were used.

(2) Preparation of cDNA

Total RNAs were extracted from the forewing bud of the pupa of *Helicoverpa armigera* (Har) 6 days after pupation, hindwing disc of the last instar larvae of *Blatta lateralis* (Bl), and the ovary and testis of adults of *Henosepilachna vigintioctopunctata* (Hy) by the hydrochloric acid guanidine method using TRIZOL (LIFE TECHNOLOGIES). Using the RNA as a template, single strand cDNAs for the 5' Rapid amplification of cDNA ends(RACE) and 3' RACE were synthesized using Superscript II reverse transcriptase (GIBCO BRL) based on SMART™ RACE cDNA Amplification Kit (CLONTECH).

(3) RT-PCR

Using the single strand cDNAs prepared as described above as templates, Polymerase chain reaction (PCR) was carried out. The Taq DNApolymerase in the PCR was Ampli Taq Gold (PERKIN ELMER). The primers used in the PCR are shown below.

```
(iap sense primer)
                                    (SEQ ID NO: 7)
iap-01: 5'-GCIGAIGCIGGITTYTWYTA-3'  (20 mer)

(SEQ ID NO: 8)
iap-02: 5'-GAYKIICCITGGGARSARCAYG-3' (22 mer)

(iap antisense primer)
                                    (SEQ ID NO: 9)
iap-03: 5'-CAIGYIRYIAIRTGICCRCAIGG-3' (23 mer)

(SEQ ID NO: 21)
iap-08: 5'-GCRCAYTTISCRCAIGCIACIAC-3' (23 mer)
``` wherein W represents A+T, S represents C+G, Y represents C+T, R represents A+G, K represents T+G, and I represents inosine. The combination of the sense primer and antisense primer and reaction conditions appropriate to the respective species are shown below.

Iap cDNA

TABLE 2

| Sample | Primer | Number of cycles | Annealing temperature (° C.) | Extension time (minutes) |
|---|---|---|---|---|
| Har | 01-03 | 50 | 45 | 0.5 |
| Har | 02-08 | 50 | 45 | 0.5 |
| Bl | 01-03 | 50 | 45 | 0.5 |
| Bl | 02-03 | 50 | 45 | 0.5 |

(4) *Henosepilachna vigintioctopunctata* 3' RACE

The procedure described in A. <Material and method> 1. (4) was carried out in the same manner, except that the samples used herein were the above-described ovary and testis of the adults.

(5) Purification of PCR Product

The procedure described in A. <Material and method> 1. (5) was carried out in the same manner.

(6) Subcloning of PCR Product into TOPO Vector (pCR4-TOPO)

The insert prepared as described above was inserted into TOPO vector (pCR4-TOPO) using TOPO TA Cloning Kit (Invitrogen). The reaction solution was used for the transformation of *Escherichia coli* (DHαTM-T1R). The culture solution of the transformed *Escherichia coli* was spread over an LB plate, and cultured at 37° C. overnight. The clone with an insert of the intended PCR fragment was selected from the formed colonies using the PCR method. The Taq DNApolymerase in the PCR was Ampli Taq Gold (PERKIN ELMER), and the primers were T3 and T7 primers. The PCR was carried out 25 cycles under conditions that denaturation (95° C., 30 seconds); annealing (55° C., 30 seconds); and extension (72° C., 30 seconds). The selected clone was cultured under shaking in an LB medium at 37° C. overnight, and a plasmid DNA was prepared using Axy Prep Plasmid Miniprep Kit (Axygen Scientific) according to the protocol of the kit.

(7) Sequencing

The procedure described in A. <Material and method> 1. (7) was carried out in the same manner.

2. RNAi Method (1) Amplification of Template for RNA Synthesis

The iap of *Helicoverpa armigera* and *Blatta lateralis* were prepared by subcloning the RT-PCR product amplified with the iap1 and iap3 primers into TOPO vector (pCR4-TOPO). In order to obtain the PCR product used as a template for synthesizing a double strand RNA, the following PCR primers containing the T7 RNA polymerase promoter sequence were used, so as to be useful for any of the genes cloned into the above-described vector.

```
(T7-PCR4R primer)
                                    (SEQ ID NO: 22)
5'-TAATACGACTCACTATAGGGAGACCACCGAATTGAATIIAGCGGC-
3'

(T7-PCR4L primer)
                                    (SEQ ID NO: 23)
5'-TAATACGACTCACTATAGGGAGACCACGTCCTGCAGGTTTAAACG-
3'
```

The PCR was carried out under the following conditions. In order to obtain a sufficient amount of PCR product, 4 to 8 pieces of the following reaction tube were provided.

| (Reaction solution) | |
|---|---|
| Template DNA (20 to 50 ng) + H$_2$O | 37.75 μl |
| 10 × buffer | 5 μl |
| 2 mM dNTP | 5 μl |
| 10 pmol/μl T7-PCR4R primer | 1 μl |
| 10 pmol/μl T7-PCR4L primer | 1 μl |
| AmpliTaq Gold (Perkin Elmer) | 0.25 μl |
| Total | 50 μl |

(Temperature Cycle)

[95° C. for 9 minutes]→[94° C. for 60 seconds→55° C. for 30 seconds→72° C. for 30 seconds]×40 cycles→72° C. for 7 minutes→12° C. for ∝

The PCR product obtained by the above reaction was concentrated by ethanol precipitation, and then subjected to agarose electrophoresis, and purified from the gel using Mag Extractor (Toyobo).

(2) Synthesis of Double Strand RNA

RNA was synthesized using 1 μs of the above-described template DNA according to MEGA script T7 Kit (Ambion), and dissolved in an adequate amount of ultrapure water free of nuclease. In order to anneal the double strand RNA, the RNA solution thus obtained was incubated at 65° C. for 30 minutes using a heating block, and returned to room temperature over a period of 1 to 2 hours. A small amount of the double strand RNA was subjected to concentration determination and agarose electrophoresis. After confirmation of the synthesis, the double strand RNA was adjusted to a concentration of 2 μg/μl for *Helicoverpa armigera* iap (Har-iap) or 10 μg/μl for *Blatta lateralis* iap (Bl-iap), divided into individual batches, and stored at −80° C.

(3) Ingestion of Double Strand RNA

For *Helicoverpa armigera*, second instar larvae was used in the experiment. 1 μl (10 μg) of Har-iap dsRNA was added to a small amount of artificial feed (Insecta LFS, Nosan Corporation). The feed was given to the larvae. GFP dsRNA was also used in the same manner. Thereafter, the larvae was observed over time.

The experiment on *Blatta lateralis* used first instar larvae. 1 μl (5 μg) of Bl-iap dsRNA aqueous solution was given. DsRed dsRNA was given to the control group in the same manner. Thereafter, the larvae was observed over time.

<Results>

1. *Henosepilachna vigintioctopunctata*

A full length cDNA sequence (SEQ ID NO: 16) coding the IAP was identified.

2. *Helicoverpa armigera* (Lepidoptera, Noctuidae)

The larvae (test group) ingested the artificial feed containing Har-iap dsRNA were observed over time. As shown in FIG. 4, all the larvae of the test group died in 4 days. The larvae of the control group were living after a lapse of 4 days. These results indicate that rapid and marked pest control effect is achieved by the IAP inhibition.

3. *Blatta lateralis*

The larvae (test group) ingested the Bl-iap dsRNA aqueous solution were observed over time. The larvae of the test group showed behavior disorder in a markedly early stage (FIG. 5). In addition, most of the larvae of the test group dead within one day. On the other hand, the larvae of the control group showed no behavior disorder or growth inhibition. These results indicate that rapid and marked pest control effect is achieved by the IPA inhibition.

C. Study of Pest Control Effect 3 (Influence of Inhibitor of Apoptosis Protein RNA Synthesized in Plant Leaves on *Henosepilachna vigintioctopunctata*)

In order to confirm that the present method is effective for the case using a transgenic plant (-derived RNA), the RNA extracted from the leaves of *Nicotiana benthamiana*, in which the iap (Hv-iap) of *Henosepilachna vigintioctopunctata* had been expressed by a virus vector, was given to *Henosepilachna vigintioctopunctata*.

<Material and Method>

(1) Test Plant

*Nicotiana benthamiana* was obtained from Leaf Tobacco Research Center, Japan Tobacco Inc. The seeds were sowed in a polyethylene pot containing Kureha Soil (Kureha Corporation) and Soil Mix (Sakata Seed Corporation), then, 10-day-old seeding was transplanted into similar polyethylene pot, and grown in a temperature-controlled room at 25° C. under light for 24 hours. The treated plant bodies were transferred to a temperature-controlled room at 22° C., and allowed to stand under light for 16 hours and in the dark for 8 hours.

(2) Test Insects

*Henosepilachna vigintioctopunctata*

(3) Extraction of Total RNA

Extraction of total RNA was carried out using TRIZOL Reagent (Invitrogen) by the following method. About 100 mg of leave tissues of *N. benthamiana* was placed in a 2-ml sampling tube (Kabushiki Kaisha Assist) containing two zirconia beads, frozen with liquid nitrogen, and fractured using Shake Master (Bio Medical Science). To the tube, 1 ml of TRIZOL Reagent was added and thoroughly suspended. The suspension was centrifuged (12,000×g, 10 minutes, 4° C.), and the upper layer was transferred to a new 1.5-ml Eppendorf tube. Two hundred μl of chloroform was added to the solution and stirred, and then centrifuged (12,000×g, 15 minutes, 4° C.). The upper layer was transferred to a new 1.5-ml Eppendorf tube, and 500 μl of isopropanol solution was added to the solution, and stirred. After standing for 10 minutes, centrifuged (12,000×g, 10 minutes, 4° C.). The precipitate thus obtained was washed with 70% ethanol, air-dried for 10 minutes, and then dissolved in 40 μl of DEPC-treated water to obtain total RNA. The $A_{260}$ was measured using a spectrophotometer (ND-1000 Spectrophotometer, NanoDrop), thereby determining the quantity of RNA, and the RNAs were used for the experiment.

(4) Preparation of Potato Virus X (PVX) Vector

The 389 bp Hv-iap cDNA fragment to be inserted into the PGR107 binary vector (Ratcliff, F., Martin-Hernandez, A. M., and Baulcombe, D. C. (2001), Tobacco rattle virus as a vector for analysis of gene function by silencing. Plant J. 25, 237-245.) containing PVX (potato virus X) was prepared by PCR. The following PCR primers containing a restriction enzyme sequence were added.

```
(Hv-iap-NotI-sense primer)
                                       (SEQ ID NO: 24)
5'-ATAAGAATGCGGCCGCGCGGAGGCGGGGTTTTATTAC-3'

(Hv-iap-NotI-antisense primer)
                                       (SEQ ID NO: 25)
5'-ATAGTTTAGCGGCCGCCAGGCGATGAGATGGCCACA-3'
```

The PCR was carried out under the following conditions. In order to obtain a sufficient amount of PCR product, two pieces of the following reaction tube were provided.

| (Reaction solution) | |
|---|---|
| Template DNA (20 to 50 ng) + H₂O | 37.75 ml |
| 10 × buffer | 5 ml |
| 2 mM dNTP | 5 ml |
| 10 pmol/μl Hv-iap-NotI-senseprimer | 1 ml |
| 10 pmol/μl Hv-iap-NotI-antisense primer | 1 ml |
| AmpliTaq Gold (Perkin Elmer) | 0.25 ml |
| Total | 50 ml |

(Temperature Cycle)

[95° C. for 9 minutes]→[94° C. for 60 seconds→55° C. for 30 seconds→72° C. for 30 seconds]×25 cycles→72° C. for 7 minutes→12° C. for ∝

The PCR product obtained by the above reaction was concentrated by ethanol precipitation, and then subjected to agarose electrophoresis, and purified from the gel using Mag Extractor (Toyobo). The cDNA fragment thus obtained was digested with NotI, incorporated into pGR107 (Ratctliff et al. 2001), and used to transform *Escherichia coli*. The *Escherichia coli* was cultured, and plasmid DNA was purified.

(5) Transformation of *A. tumefaciens* by Electroporation

The transformation of *Agrobacterium tumefaciens* was carried out according to the method of Hellens et al, (Hellens, R. P., Edwards, E. A., Leyland, N. R., Bean, S., and Mullineaux, P. M. (2000). pGreen: A versatile and flexible binary Ti vector for *Agrobacterium*-mediated plant transformation Plant Mol. Biol. 42, 819-832). Forty μl of *A. tumefaciens* GV3101 was mixed with the vector to be introduced (10 ng) and a helper plasmid pSoup (10 ng), and dissolved on ice, and the electro-cell was allowed to stand on ice for 30 minutes. The solution was transferred to a cuvette which had been cooled on ice, and transformation was carried out through electroporation using a gene introduction apparatus Micro Pulser™ (BIO-RAD) (V=1.44 kV, T=2.5 kV/resistance, C=all out, R=R5 129). The solution was transferred to a 14-ml polypropylene round-bottom tube (BECTON DICKINSON), allowed to stand on ice for 10 minutes. Thereafter, 960 μl of SOC medium [2% trypton peptone, 0.5% yeast extract, 0.05% NaCl, 10 mM $MgCl_2$, 10 mM $MgSO_4$, 20 mM glucose, pH 7.0] was added, and shaken at 28° C. for 1 hour. 20 μl of the solution was spread over a YEB medium [0.1% yeast extract, 0.5% beef extract, 0.5% trypton peptone, 0.5% sucrose, 2 mM $MgSO_4$, 2% agar, pH 7.2] containing kanamycin (50 μg/ml) and rifampicin (50 μg/ml), and cultured at 28° C. for 30 hours.

(6) High Expression of Hv-iap by Virus Vector

*Agrobacterium* retaining pGR107 vector containing a 389 bp Hv-iap cDNA fragment was cultured at 28° C. for 2 days in an LB liquid medium containing 50 μg/ml of kanamycin, 50 μg/ml of rifampicin, and 5 μg/ml of tetracycline. The culture solution was diluted 5 to 10 folds with an LB liquid medium, and further cultured at 28° C. until $OD_{600}$=0.5-1.0. *Agrobacterium* was collected by centrifugation (1,700×g, 15 minutes), suspended in 5 ml of loading buffer solution, and the bacterium was collected again by centrifugation. The precipitated *Agrobacterium* was suspended in a loading buffer solution containing 150 μM acetosyringone so as to $OD_{600}$=0.5, and allowed to stand at room temperature for 2 hours. Thereafter, the solution was injected using an injection tube into the intercellular space of the *N. benthamiana* leaves after a lapse of about 3 weeks from the seeding. The upper leaves of the plant after a lapse of 3 to 4 weeks from the injection of *Agrobacterium* were used for the experiment.

(7) RT-PCR

RT-PCR was carried out as follows using ReverTra Ace-Plus-(registered trademark) (TOYOBO). 6 μl of the solution was mixed with 0.5 μg of total RNA and 25 pmol of Oligo(dT) 20 primer, treated at 65° C. for 5 minutes, and then immediately cooled on ice. Subsequently, the remaining RT-PCR reaction solution [1×RT reaction solution, 1 mM dNTPs, 1 unit/μl RNase inhibitor, 5 unit/μl ReverTra Ace (registered trademark)] was added, and reverse transcription reaction was carried out in 10 μl of the reaction solution at 30° C. for 10 minutes, at 42° C. for 1 hour, and at 85° C. for 5 minutes. The PCR reaction was carried out using ExTaq (Takara) in 10 μl of the reaction solution for 1 μl of the reverse transcription reaction solution, and consisted of 27 cycles of annealing at 53° C. for 20 seconds, and extension at 74° C. for 30 seconds.

The base sequences of the primers used for the RT-PCR are shown below.

```
(Hv-iap-NotI-sense primer)
                                        (SEQ ID NO: 24)
5'-ATAAGAATGCGGCCGCGCGGAGGCGGGGTTTTATTAC-3'

(Hv-iap-NotI-anti sense primer)
                                        (SEQ ID NO: 25)
5'-ATAGTTTAGCGGCCGCCAGGCGATGAGATGGCCACA-3'

(EF-1α sense primer)
                                        (SEQ ID NO: 26)
5'-TGTGGAAGTTTGAGACCACC-3'

(EF-1α anti sense primer)
                                        (SEQ ID NO: 27)
5'-GCAAGCAATGCGTGCTCAC-3'
```

(8) Amplification of Template for RNA Synthesis and Synthesis of dsRNA

The iap (Hv-iap) of *Henosepilachna vigintioctopunctata* was the same as that used in A. <Material and method> 2. (1) and (2).

(9) Ingestion of Leaf-Extracted RNA and Synthetic dsRNA

The third instar larvae of *Henosepilachna vigintioctopunctata* were used for the experiment. *Henosepilachna vigintioctopunctata* does not ingest the leaves of *N. benthamiana* which is not its food plant. Therefore, the effects of the Hv-iap dsRNA and siRNA which are likely contained in the RNA expressed in the plant were studied. The total RNA was extracted from *N. benthamiana* leaves wherein a virus containing an Hv-iap gene fragment had been expressed, and 2 μg of the total RNA was given to the larvae. To the control group, 2 μg of the total RNA extracted from the *N. benthamiana* leaf tissues wherein a virus alone was expressed. After the ingestion, the potato leaves were given to the larvae. In addition, the amount of the Hv-iap dsRNA contained in the total RNA extracted from the leave tissues of *N. benthamiana* is likely very small, so that Hv-iap synthetic dsRNA was used as the positive control. In this case, after ingestion of 20 ng, the potato leaves were given to the larvae. Thereafter, the larvae were observed over time.

<Result>

The larvae ingested the total RNA extracted from the leaves of *N. benthamiana* wherein the virus with Hv-iap dsRNA had expressed (test group) almost stopped ingestion after a lapse of 43 hours except for one individual, and completely stopped ingestion after a lapse of 67 hours (FIG. 6). These results indicate that the inhibitory effect against IAP is sufficiently achieved even when the RNA is synthesized in a plant. It was also strongly suggested that the transformation of a plant body (more specifically, creation of a transgenic plant) so as to specifically inhibit the expression of IAP of the target pest is effective as a pest control strategy. It should be also noted that the ingestion was sufficiently stopped even when a very small amount (20 ng) of dsRNA was ingested (positive control).

INDUSTRIAL APPLICABILITY

The pest control method of the present invention inhibits IAP by incorporating an IAP inhibitor into the body of the pest, thereby achieving pest control effect. The present invention is versatile and applicable to various pests. In addition, the present invention is applicable to pests in various developmental stages.

The present invention is not limited to the above-described explanations of the embodiments and examples. Various modifications readily appreciated by those skilled in the art are also included in the present invention, without departing from the scope of the description of claims.

The articles, unexamined patent publications, and published unexamined patent applications cited in the present description are hereby incorporated by reference herein in their entirety.

[Sequence List Free Text]

SEQ ID NO: 7: explanation for artificial sequence: iap sense primer (iap-01)

SEQ ID NO: 8: explanation for artificial sequence: iap sense primer (iap-02)

SEQ ID NO: 9: explanation for artificial sequence: iap antisense primer (iap-03)

SEQ ID NO: 10: explanation for artificial sequence: primer for 5' RACE (Hv-iap-01)

SEQ ID NO: 11: explanation for artificial sequence: primer for 5' RACE (Hv-iap-02)

SEQ ID NO: 12: explanation for artificial sequence: primer for 3' RACE (Hv-iap-03)

SEQ ID NO: 13: explanation for artificial sequence: primer for 3' RACE (Hv-iap-04)

SEQ ID NO: 14: explanation for artificial sequence: primer for PCR (T7-KS)

SEQ ID NO: 15: explanation for artificial sequence: primer for PCR (T7-SK)

SEQ ID NO: 21: explanation for artificial sequence: iap antisense primer (iap-08)

SEQ ID NO: 22: explanation for artificial sequence: primer for PCR (T7-PCR4R)

SEQ ID NO: 23: explanation for artificial sequence: primer for PCR (T7-PCR4L)

SEQ ID NO: 24: explanation for artificial sequence: Hv-iap-NotI-sense primer

SEQ ID NO: 25: explanation for artificial sequence: Hv-iap-NotI-antisense primer SEQ ID NO: 26: explanation for artificial sequence: EF-1α sense primer SEQ ID NO: 27: explanation for artificial sequence: EF-1α antisense primer

---

The invention claimed is:

1. A pest control method comprising incorporating an inhibitor against inhibitor of apoptosis (IAP) into the body of a target pest,
wherein the inhibitor is a compound selected from the group consisting of the following (a) to (d):
(a) an siRNA targeted at a gene coding the inhibitor of apoptosis of the target pest;
(b) a nucleic acid construct intracellularly producing an siRNA targeted at a gene coding the inhibitor of apoptosis of the target insect;
(c) an antisense nucleic acid targeted at the transcript product of a gene coding the inhibitor of apoptosis of the target pest; and
(d) a ribozyme targeted at the transcript product of a gene coding the inhibitor of apoptosis of the target pest; and
wherein the gene includes the sequence set forth in SEQ ID NO: 1, the sequence set forth in SEQ ID NO: 3, the sequence set forth in SEQ ID NO: 5, the sequence set forth in SEQ ID NO: 16, the sequence set forth in SEQ ID NO: 17, or the sequence set forth in SEQ ID NO: 19.

2. The pest control method according to claim 1, comprising making a plant, which is to be attacked by the target pest, possess an agent containing the inhibitor by application, spraying, or atomization in advance, and incorporating the inhibitor into the body of the target pest by ingestion of the plant.

3. The pest control method according to claim 1, comprising placing a feed containing the inhibitor at the site of occurrence or in the route of entry of the target pest, and incorporating the inhibitor into the body of the target pest by ingestion of the feed.

4. The pest control method according to claim 1, comprising incorporating the inhibitor into the body of the target pest by ingestion of a transgenic plant containing a gene coding the inhibitor.

5. A pest control agent comprising an inhibitor against inhibitor of apoptosis of the target pest,
wherein the inhibitor is a compound selected from the group consisting of the following (a) to (d):
(a) an siRNA targeted at a gene coding the inhibitor of apoptosis of the target pest;
(b) a nucleic acid construct intracellularly producing an siRNA targeted at a gene coding the inhibitor of apoptosis of the target insect;
(c) an antisense nucleic acid targeted at the transcript product of a gene coding the inhibitor of apoptosis of the target pest; and
(d) a ribozyme targeted at the transcript product of a gene coding the inhibitor of apoptosis of the target pest; and
wherein the gene includes the sequence set forth in SEQ ID NO: 1, the sequence set forth in SEQ ID NO: 3, the sequence set forth in SEQ ID NO: 5, the sequence set forth in SEQ ID NO: 16, the sequence set forth in SEQ ID NO: 17, or the sequence set forth in SEQ ID NO: 19.

6. A transgenic plant comprising a gene coding an inhibitor against inhibitor of apoptosis of a target pest,
wherein the inhibitor is a compound selected from the group consisting of the following (a) to (d):
(a) an siRNA targeted at a gene coding the inhibitor of apoptosis of the target pest;
(b) a nucleic acid construct intracellularly producing an siRNA targeted at a gene coding the inhibitor of apoptosis of the target insect;
(c) an antisense nucleic acid targeted at the transcript product of a gene coding the inhibitor of apoptosis of the target pest; and
(d) a ribozyme targeted at the transcript product of a gene coding the inhibitor of apoptosis of the target pest; and
wherein the gene includes the sequence set forth in SEQ ID NO: 1, the sequence set forth in SEQ ID NO: 3, the sequence set forth in SEQ ID NO: 5, the sequence set forth in SEQ ID NO: 16, the sequence set forth in SEQ ID NO: 17, or the sequence set forth in SEQ ID NO: 19.

* * * * *